US008084145B2

(12) United States Patent
Inoue et al.

(10) Patent No.: US 8,084,145 B2
(45) Date of Patent: Dec. 27, 2011

(54) ORGANOMETALLIC COMPLEX, LIGHT EMITTING ELEMENT USING THE COMPLEX, LIGHT EMITTING DEVICE USING THE ELEMENT, AND ELECTRIC APPARATUS USING THE DEVICE

(75) Inventors: Hideko Inoue, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 802 days.

(21) Appl. No.: 11/092,816

(22) Filed: Mar. 29, 2005

(65) Prior Publication Data

US 2005/0221123 A1 Oct. 6, 2005

(30) Foreign Application Priority Data

Apr. 2, 2004 (JP) ................................. 2004-110133

(51) Int. Cl.
*H01L 51/54* (2006.01)
*C09K 11/06* (2006.01)

(52) U.S. Cl. . 428/690; 428/917; 313/504; 257/E51.044; 544/225

(58) Field of Classification Search .................. None
See application file for complete search history.

(56) References Cited

U.S. PATENT DOCUMENTS

| | | | |
|---|---|---|---|
| 5,484,922 A | 1/1996 | Moore et al. | |
| 6,780,528 B2 | 8/2004 | Tsuboyama et al. | |
| 6,821,646 B2 | 11/2004 | Tsuboyama et al. | |
| 6,953,628 B2 | 10/2005 | Kamatani et al. | |
| 7,094,477 B2 | 8/2006 | Kamatani et al. | |
| 7,147,935 B2 | 12/2006 | Kamatani et al. | |
| 7,220,495 B2 | 5/2007 | Tsuboyama et al. | |
| 7,527,879 B2 | 5/2009 | Kamatani et al. | |
| 7,544,426 B2 | 6/2009 | Kamatani et al. | |
| 7,569,692 B2 | 8/2009 | Nii et al. | |
| 7,589,203 B2 | 9/2009 | Stössel et al. | |
| 7,687,155 B2 | 3/2010 | Kamatani et al. | |
| 7,709,100 B2 | 5/2010 | Kwong et al. | |
| 7,883,785 B2 | 2/2011 | Stossel et al. | |
| 2001/0019782 A1* | 9/2001 | Igarashi et al. | 428/690 |
| 2002/0121638 A1* | 9/2002 | Grushin et al. | 257/40 |
| 2003/0059646 A1* | 3/2003 | Kamatani et al. | 428/690 |
| 2006/0127696 A1 | 6/2006 | Stossel et al. | |
| 2006/0177694 A1 | 8/2006 | Kamatani et al. | |
| 2006/0228583 A1 | 10/2006 | Kamatani et al. | |
| 2007/0129545 A1 | 6/2007 | Inoue et al. | |
| 2007/0212570 A1 | 9/2007 | Kamatani et al. | |
| 2007/0216294 A1 | 9/2007 | Kamatani et al. | |
| 2009/0015143 A1 | 1/2009 | Inoue et al. | |
| 2009/0174324 A1 | 7/2009 | Nii et al. | |
| 2009/0184634 A1 | 7/2009 | Kamatani et al. | |

FOREIGN PATENT DOCUMENTS

| | | |
|---|---|---|
| CN | 1478372 A | 2/2004 |
| CN | 1678617 A | 10/2005 |
| EP | 1 191 612 A2 | 3/2002 |
| EP | 1 191 614 A2 | 3/2002 |
| EP | 1 348 711 A1 | 10/2003 |
| EP | 1 349 435 A1 | 10/2003 |
| EP | 1 881 050 A2 | 1/2008 |
| EP | 1 889 891 A2 | 2/2008 |
| JP | 48-8788 A | 2/1973 |
| JP | 2002-105055 | 4/2002 |
| JP | 2002-175884 | 6/2002 |
| JP | 2003-81988 | 3/2003 |
| WO | WO 02/45466 A1 | 6/2002 |
| WO | WO 2004/108857 A1 | 12/2004 |
| WO | WO 2005/115061 A1 | 12/2005 |

OTHER PUBLICATIONS

Shavaleev et al., "Sensitized Near-Infrared Emission from Complexes . . . ", Chem. Eur. J. 9(21), pp. 5283-5291 (2003).*
Zhang, G.L. et al., "Synthesis and Luminescence Property of a New Yellow Phosphorescent Iridium (III) Pyrazine Complex", Chemical Journal of Chinese Universities, vol. 25, No. 3, pp. 397-400, Mar. 2004, English language translation.
Zhang, G.L. et al, "Synthesis and Luminescence Property of a New Yellow Phosphorescent Iridium (III) Pyrazine Complex," Chemical Journal of Chinese Universities, vol. 25, No. 3, pp. 397-400, Mar. 2004; English abstract.
Steel, P.J. et al., "Cyclometallated Compounds, V. Double Cyclopalladation of Diphenyl Pyrazines and Related Ligands" Journal of Organometallic Chemistry, vol. 395, No. 3, 1990, pp. 359-373.
Slater, J.W. et al., "Cyclometallated Nitrogen Heterocycles," Journal of Organometallic Chemistry, vol. 688, 2003, pp. 112-120.
Tsutsui, T. et al., "High Quantum Efficiency in Organic Light-Emitting Devices with Iridium-Complex as a Triplet Emissive Center," Japanese Journal of Applied Physics, Dec. 15, 1999, vol. 38, No. 12B, pp. L1502-L1504.

(Continued)

*Primary Examiner* — Marie R. Yamnitzky
(74) *Attorney, Agent, or Firm* — Husch Blackwell LLP

(57) ABSTRACT

An organometallic complex comprising a moiety represented by the following general formula (1). The organometallic complex is applied to a light-emitting element, and a light-emitting device reduced in power consumption is manufactured by using the light-emitting element.

[formula 1]

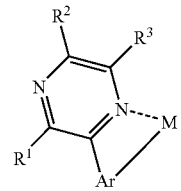

(where $R^1$ to $R^4$ are individually any one of hydrogen, a halogen atom, an acyl group, an alkyl group, an alkoxyl group, an aryl group, a cyano group, and a heterocyclic group, Ar is one of an aryl group having an electron-withdrawing group and a heterocyclic group having electron-withdrawing group, and M is one of an element of Group 9 and an element of Group 10)

34 Claims, 22 Drawing Sheets

OTHER PUBLICATIONS

O'Brien, D. et al., "Improved Energy Transfer in Electrophosphorescent Devices," Applied Physics Letters, vol. 74, No. 3, Jan. 18, 1999, pp. 442-444.

Baldo, M. et al., "High-Efficiency Fluorescent Organic Light-Emitting Devices Using a Phosphorescent Sensitizer," Nature, vol. 403, Feb. 17, 2000, pp. 750-753.

Tsutsui, T. "Mechanism of Organic EL Element and Luminous Efficiency," Textbook of the 3rd Seminar at Division of Organic Molecular Electronics and Bioelectronics, 1993, pp. 31-37, Division of Molecular Electronics and Bioelectronics, The Japan Society of Applied Physics.

Inoue, H. et al., "A Reaction of Singlet Oxygen with an Unsaturated Organic Molecule, 6.1.4, Quencher and Photosensitizer," Basic Chemistry Course Photochemistry I, Maruzen Co., Ltd., publishers Sep. 30, 1999, pp. 106-110.

Thompson, M. et al., "Phosphorescent Materials and Devices," Proceedings of the 10th International Workshop on Inorganic and Organic Electroluminescence (EL'00), Dec. 4, 2000, pp. 35-38.

Duan, J.-P. et al., "New Iridium Complexes as Highly Efficient Orange-Red Emitters in Organic Light-Emitting Diodes," Advanced Materials, vol. 15, No. 3, Feb. 5, 2003, pp. 224-228.

Zhang, L. et al, "Synthesis and Phosphorescence Property of a New Pyrazine Iridium(III) Complex," Acta Phys.-Chim. Sin., vol. 19, No. 10, 2003, pp. 889-891(with English translation).

International Search Report re Application No. PCT/JP2006/323882, Dated Jan. 16, 2007.

Written Opinion re Application No. PCT/JP2006/323882, Dated Jan. 16, 2007.

International Search Report re Application No. PCT/JP2006/305474, Dated Apr. 11, 2006.

Written Opinion re Application No. PCT/JP2006/305474, Dated Apr. 11, 2006.

Usyatinsky, A. Ya., et al, "Microwave-Assisted Synthesis of Substituted Imidazoles on a Solid Support Under Solvent-Free Conditions," Tetrahedron Letters, vol. 41, No. 26, 2000, pp. 5031-5034.

Kidwai, M. et al, "Microwave Assisted Synthesis of Novel 1,2,4-Triazines in 'Dry Media'," Synthetic Communications, vol. 31, No. 11, 2001, pp. 1639-1645.

Konno, H. et al, "Selective One-Pot Synthesis of Facial Tris-Ortho-Metalated Iridium(III) Complexes Using Microwave Irradiation," Chemistry Letters, vol. 32, No. 3, 2003, pp. 252-253, The Chemical Society of Japan.

Slater, J.W. et al., "Cyclometallated Nitrogen Heterocycles," Journal of Organometallic Chemistry, vol. 688, Aug. 29, 2003, pp. 112-120.

European Search Report re application No. EP 07005200.6, dated Jul. 23, 2007.

Office Action re U.S. Appl. No. 11/607,649, dated Feb. 3, 2010.

Declaration of Satoshi Seo, filed in U.S. Appl. No. 11/607,649, dated Jun. 1, 2010.

European Search Report re application No. EP 06715702.4, dated Jul. 23, 2010.

Final Rejection re U.S. Appl. No. 11/607,649, dated Aug. 18, 2010.

Office Action re Chinese Application No. CN 200680045339.7, dated Feb. 24, 2011, (with English Translation).

Office Action re Chinese Application No. CN 200710087859.0, dated Mar. 2, 2011, (with English Translation).

Yersin, H. et al., "Triplet Emitters for Organic Light-Emitting Diodes: Basic Properties," Highly Efficient OLEDs with Phosphorescent Materials, 2008, pp. 1-18.

European Office Action re application No. EP 06715702.4, dated Jun. 24, 2011.

\* cited by examiner

······ ABSORPTION SPECTRUM
―― EMISSION SPECTRUM
―― EXCITATION SPECTRUM

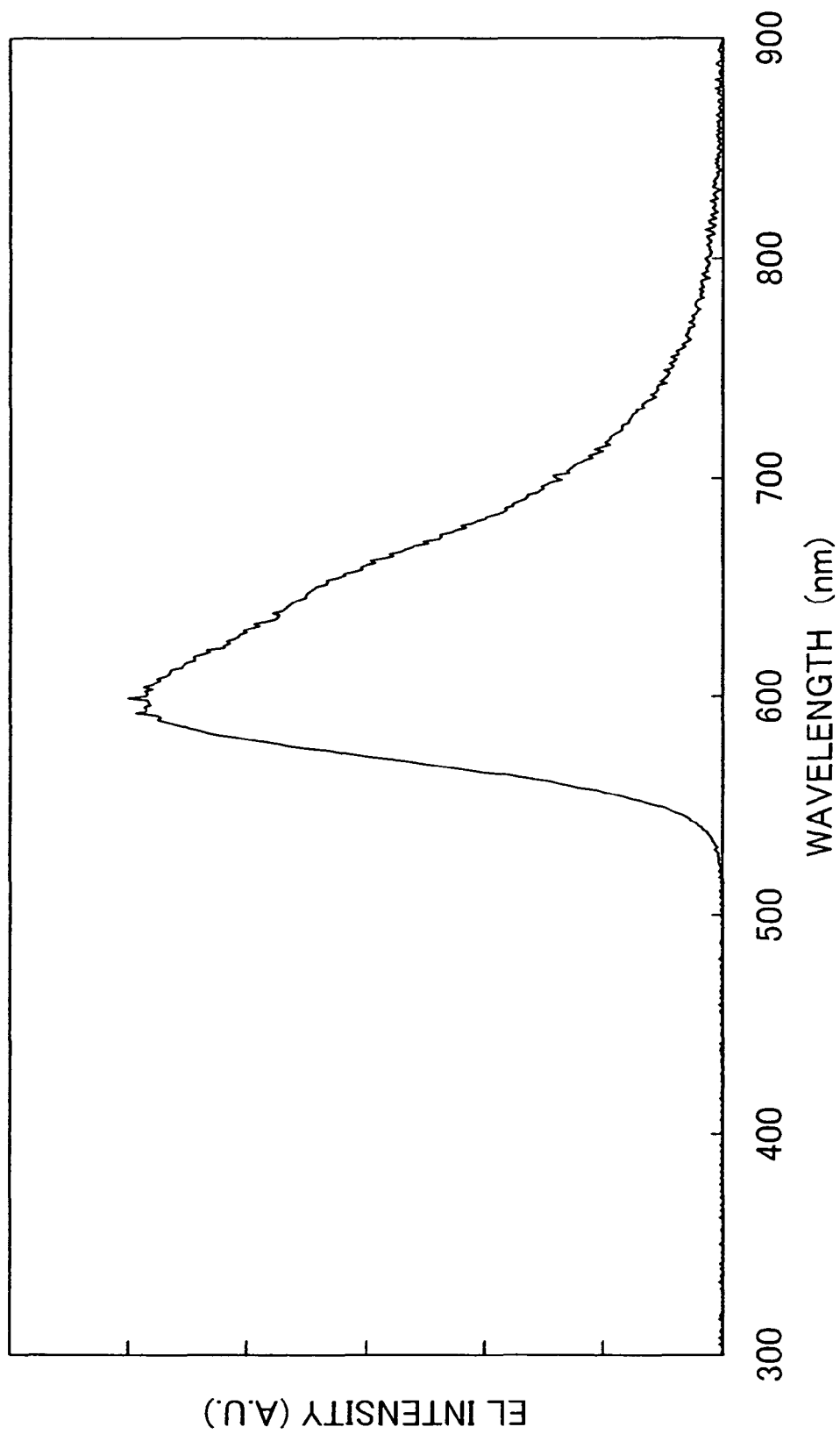

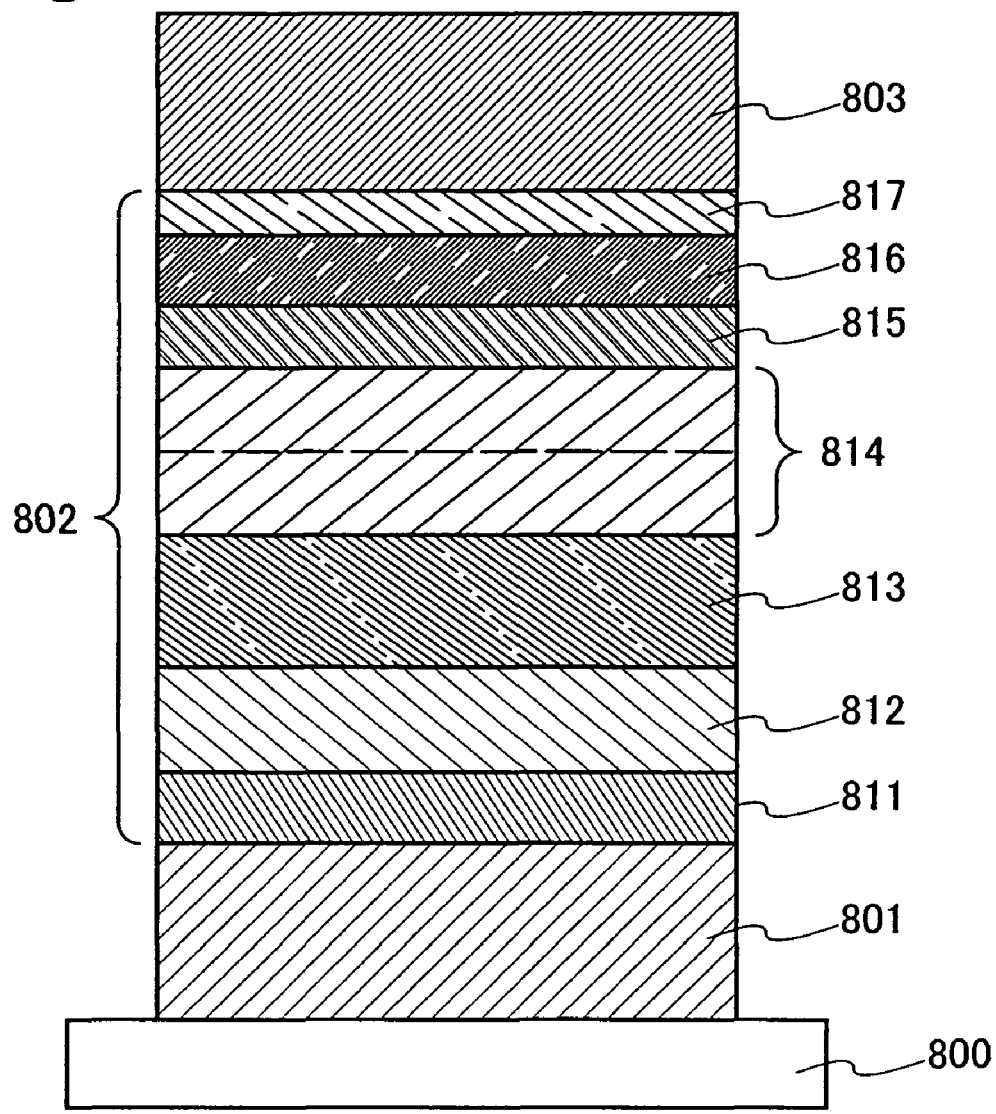

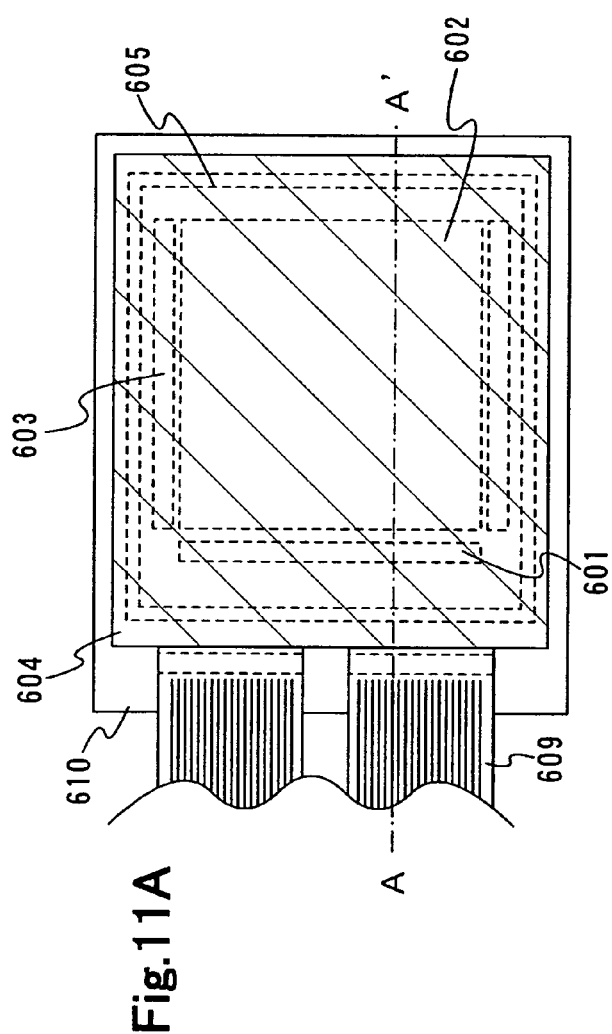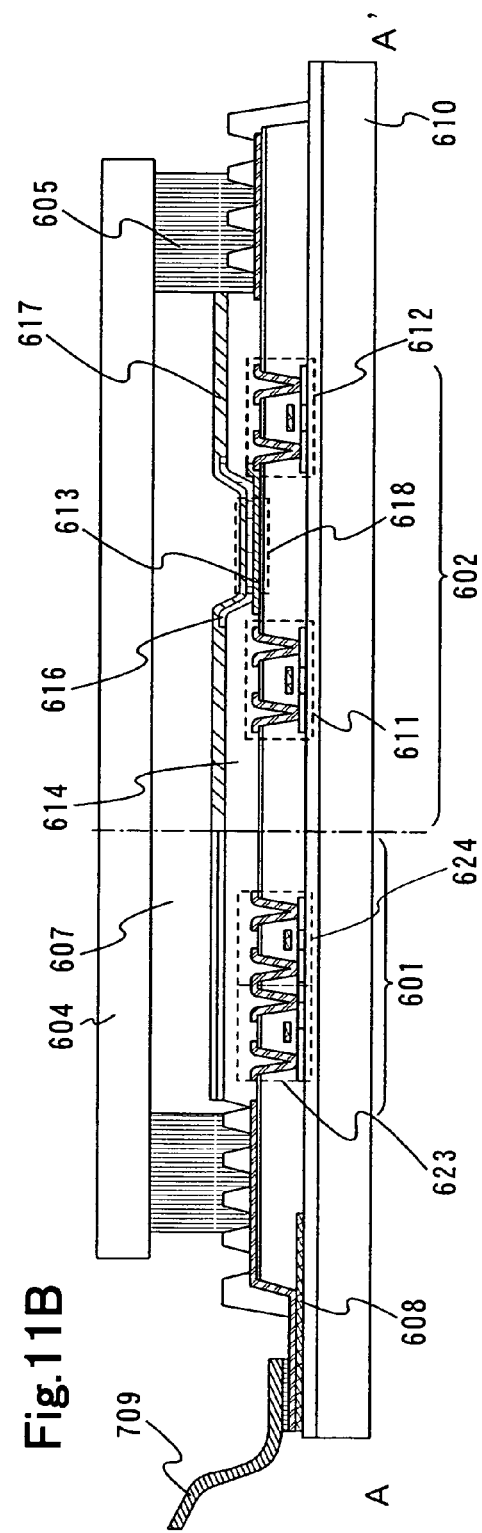
Fig.11A
Fig.11B

ORGANOMETALLIC COMPLEX, LIGHT EMITTING ELEMENT USING THE COMPLEX, LIGHT EMITTING DEVICE USING THE ELEMENT, AND ELECTRIC APPARATUS USING THE DEVICE

BACKGROUND OF THE INVENTION

1. Field of the Invention

The present invention relates to an organometallic complex, and in particular, relates to an organometallic complex that is able to convert an excited triplet state into luminescence. In addition, the present invention relates to a light-emitting element that has an anode, a cathode, and a layer including an organic compound from which luminescence can be obtained by applying an electric field (hereinafter, referred to as "a layer including a luminescent material").

2. Description of the Related Art

Organic compounds (organic molecules) are brought into a state with energy (excitation state) by absorbing light. By going through this excitation state, various reactions such as photochemical reactions are caused in some cases, or luminescence is produced in some cases. Therefore, the organic compounds have found various applications.

As one example of the photochemical reactions, a reaction (oxygen addition) of singlet oxygen with an unsaturated organic molecule is known (refer to Non-Patent Reference 1, for example). Since the ground state of an oxygen molecule is a triplet state, oxygen in a singlet state (singlet oxygen) is not generated by a direct photoexcitation. However, in the presence of another triplet-excited molecule, singlet oxygen is generated to achieve an oxygen addition reaction. In this case, a compound that is capable of forming the triplet excited molecule is referred to as a photosensitizer.

(Non-Patent Reference 1)

Haruo INOUE, et al., Basic Chemistry Course PHOTOCHEMISTRY I (Maruzen Co., Ltd.), pp. 106-110 (1999)

As described above, in order to generate singlet oxygen, a photosensitizer that is capable of forming a triplet excited molecule by photoexcitation is necessary. However, since the ground state of an ordinary organic compound is a singlet state, photoexcitation to an excited triplet state is a forbidden transition, and a triplet excited molecule is unlikely to be generated (a singlet-excited molecule is usually generated). Therefore, as such a photosensitizer, a compound in which intersystem crossing from the excited singlet state to the excited triplet state easily occurs or a compound in which the forbidden transition of photoexcitation directly to the excited triplet state is allowed is required. In other words, such a compound can be used as a photosensitizer, and is useful.

Also, such a compound often discharges phosphorescence. The phosphorescence is luminescence generated by transition between different energies in multiplicity and, in the case of an ordinary organic compound, indicates luminescence generated in returning from the excited triplet state to the singlet ground state (in contrast, luminescence in returning from an excited singlet state to a singlet ground state is referred to as fluorescence). Application fields of a compound that is capable of discharging the phosphorescence, that is, a compound that is capable of converting an excited triplet state into luminescence (hereinafter, referred to as a phosphorescent compound), include a light-emitting element using an organic compound as a luminescent compound.

This light-emitting element is a device attracting attention as a next-generation flat panel display element in terms of characteristics such as being thin and light in weight, high speed response, and direct current low voltage driving. In addition, because of being a self light emitting element and having a wide viewing angle, the light-emitting element has a comparatively favorable visibility, and is considered to be effective as an element to be used for a display screen of a mobile appliance.

In the case of using an organic compound as a light emitter, the emission mechanism of a light-emitting device is a carrier injection type. Namely, by applying a voltage with a light-emitting layer sandwiched between electrodes, an electron injected from a cathode and a hole injected from an anode are recombined in the light-emitting layer to form an exited molecule, and energy is released to emit light when the excited molecule returns to the ground state.

As the type of the excited molecule, as in the case of photoexcitation described above, an excited singlet state (S*) and an excited triplet state (T*) are possible. Further, the statistical generation ratio thereof in a light-emitting element is considered to be S*:T*=1:3 (refer to the following Non-Patent Reference 2, for example).

(Non-Patent Reference 2)

Tetsuo TSUTSUI, Textbook for the $3^{rd}$ Workshop, Division of Molecular Electronics and Bioelectronics, Japan Society of Applied Physics, pp. 31-37 (1993)

However, in the case of ordinary organic compounds, luminescence (phosphorescence) from an excited triplet state is not observed at room temperature while only luminescence from an excited singlet state (fluorescence) is usually observed. This is because $T^* \text{---} > S_0$ transition (phosphorescence process) is a strong forbidden transition and $S^* \text{---} > S_0$ transition (fluorescence process) is an allowed transition since the ground state of an organic compound is usually a singlet ground state ($S_0$).

Accordingly, the internal quantum efficiency (the ratio of photons generated to injected carriers) in a light-emitting element is assumed to have a theoretical limit of 25% in accordance with S*:T*=1:3.

However, since the $T^* \text{---} > S_0$ transition (phosphorescence process) is allowed when the phosphorescent compound described above is used, the internal quantum efficiency can be improved to 75 to 100% in theory. Namely, a luminous efficiency that is 3 to 4 times as much as that of the conventional one can be achieved. Actually, light-emitting elements using phosphorescent compounds have been reported one after another, and the luminous efficiencies thereof have been attracting attention (refer to Non-Patent References 3 and 4, for example).

(Non-Patent Reference 3)

D. F. O'Brien, et al., Applied Physics Letters, vol. 74, No. 3, pp. 442-444 (1999)

(Non-Patent Reference 4)

Tetsuo TSUTSUI, et al., Japanese Journal of Applied Physics, vol. 38, pp. L1502-L1504 (1999)

A porphyrin complex that has platinum as a central metal and an organometallic complex that has iridium as a central metal are used respectively in Non-Patent References 3 and 4, which are both phosphorescent compounds.

Further, by alternately stacking a layer including an organometallic complex that has iridium as a central metal (hereinafter, referred to as an iridium complex) and a layer including DCM2 that is a known fluorescent compound, it is possible to move triplet excitation energy generated in the iridium complex to DCM2 so as to contribute to luminescence from DCM2 (refer to Non-Patent Reference 5, for example). In this case, since the volume of the excited singlet state of DCM2 (usually 25% or less) is amplified more than usual, the luminous efficiency of DCM2 is increased. This can be said to be, in a manner, a sensitization effect of the iridium complex that is a phosphorescent compound.

(Non-Patent Reference 5)

M. A. Baldo, et al., Nature (London), vol. 403, pp. 750-753 (2000)

As described in Non-Patent References 3 to 5, a light-emitting element using a phosphorescent compound is capable of achieving a higher luminous efficiency than conventional ones (that is, capable of achieving a higher luminance with a small current). Therefore, it is considered that a light-emitting element using a phosphorescent compound will play a great role in future development as a method for achieving luminescence with a higher luminance and a higher luminous efficiency.

As described above, in phosphorescent compounds, intersystem crossing is likely to occur, and luminescence (phosphorescence) from an excited triplet state is unlikely to be produced. Therefore, phosphorescent compounds are useful in using as a photosensitizer and applying to a light-emitting element as a phosphorescent material, and expected compounds. However, the number thereof is small under the present situation.

Among the small number of phosphorescent compounds, the iridium complex used in Non-Patent Reference 4 or 5 is one kind of organometallic complexes, referred to as ortho-metalated complexes. Since this complex has a phosphorescence life of several hundreds of nanoseconds and is high in phosphorescence quantum yield, the reduction in efficiency due to increase in luminance is smaller than that of the porphyrin complex described above. Therefore, the complex is effectively used in a light-emitting element. For this reason, such an organometallic complex is one of guidelines for synthesizing a compound in which direct photoexcitation or intersystem crossing to the triplet excited state is likely to occur, and furthermore, a phosphorescent compound.

The iridium complex used in Non-Patent References 4 or 5 has a relatively simple ligand structure and shows green luminescence with favorable color purity. However, it is necessary to change the ligand structure in order to change the luminescent color to a different one. For example, in Non-Patent Reference 6, various ligands and iridium complexes using the ligands are synthesized, and several luminescent colors are realized.

(Non-Patent Reference 6)

Mark E. Thompson, et al., The 10$^{th}$ International workshop on Inorganic and Organic Electroluminescence (EL'00), pp. 35-38 (2000)

However, since these are very limited examples, and insufficient satisfaction is obtained as for the kinds thereof. The organometallic complexes described above are materials in which intersystem crossing is likely to occur, and versatile application such as a photosensitizer and a phosphorescent material can be considered. Therefore, versatile performance is required depending on the application.

Accordingly, novel organometallic complexes in which intersystem crossing to an excited triplet state is likely to occur are desired. Above all, a novel organometallic complex that can be used as a phosphorescent material is desired in order to obtain a particularly high-efficiency light-emitting element.

SUMMARY OF THE INVENTION

It is an object of the present invention to provide a novel phosphorescent organometallic complex in which intersystem crossing to an excited triplet state is likely to occur. In addition, it is also an object of the present to provide a high-efficiency light-emitting element using the organometallic complex. Further, it is also an object of the present invention to provide a light-emitting device reduced in power consumption and using the light-emitting element.

A lot of diligent experiments and studies by the inventors have finally found that an organometallic complex including a moiety represented by the following general formula (1) is a phosphorescent compound in which intersystem crossing to an excited triplet state is likely to occur.

[formula 1]

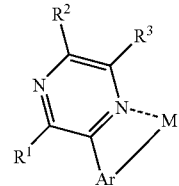

(where $R^1$ to $R^3$ are individually any one selected from the group consisting of hydrogen, a halogen atom, an acyl group, an alkyl group, an alkoxyl group, an aryl group, a cyano group, and a heterocyclic group, Ar is one of an aryl group having an electron-withdrawing group and a heterocyclic group having electron-withdrawing group, and M is one of an element of Group 9 and an element of Group 10)

Accordingly, the present invention provides an organometallic complex including a moiety represented by the general formula (1). Above all, an organometallic complex including a moiety represented by the following general formula (2) is particularly preferable.

[formula 2]

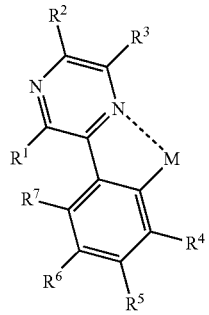

(where $R^1$ to $R^3$ are individually any one selected from the group consisting of hydrogen, a halogen atom, an acyl group, an alkyl group, an alkoxyl group, an aryl group, a cyano group, and a heterocyclic group, any one (at least one) of $R^4$ to $R^7$ is an electron-withdrawing group, the others of $R^4$ to $R^7$ are individually any one of hydrogen, a halogen atom, an acyl group, an alkyl group, an alkoxyl group, an aryl group, a cyano group, and a heterocyclic group, and M is one of an element of Group 9 and an element of Group 10)

In addition, of organometallic complexes including a moiety represented by the general formula (1), an organometallic complex including a moiety represented by the following general formula (3) is particularly preferable.

[formula 3]

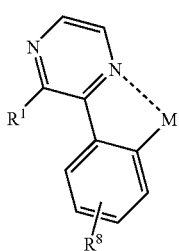

(where $R^1$ is any one selected from the group consisting of hydrogen, a halogen atom, an acyl group, an alkyl group, an alkoxyl group, an aryl group, a cyano group, and a heterocyclic group, $R^8$ is an electron-withdrawing group, and M is one of an element of Group 9 and an element of Group 10)

Also, the inventors have found that an organometallic complex represented by the following general formula (4) is a phosphorescent compound in which intersystem crossing to an excited triplet state is likely to occur.

[formula 4]

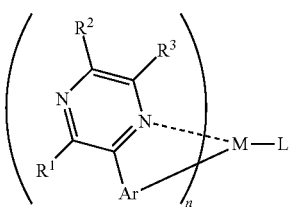

(where $R^1$ to $R^3$ are individually any one selected from the group consisting of hydrogen, a halogen atom, an acyl group, an alkyl group, an alkoxyl group, an aryl group, a cyano group, and a heterocyclic group, Ar is one of an aryl group having an electron-withdrawing group and a heterocyclic group having electron-withdrawing group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

Accordingly, the present invention provides an organometallic complex represented by the general formula (4). Above all, an organometallic complex represented by the following general formula (5) is particularly preferable.

[formula 5]

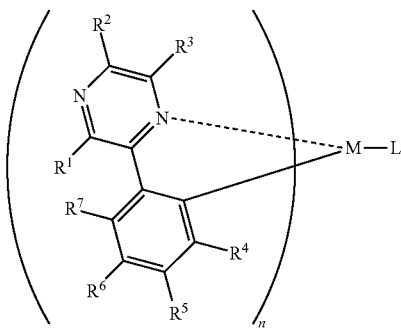

(where $R^1$ to $R^3$ are individually any one selected from the group consisting of hydrogen, a halogen atom, an acyl group, an alkyl group, an alkoxyl group, an aryl group, a cyano group, and a heterocyclic group, any one (at least one) of $R^4$ to $R^7$ is an electron-withdrawing group, the others of $R^4$ to $R^7$ are individually any one selected form the group consisting of hydrogen, a halogen atom, an acyl group, an alkyl group, an alkoxyl group, an aryl group, a cyano group, and a heterocyclic group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

In addition, of organometallic complexes represented by the general formula (4), an organometallic complex represented by the following general formula (6) is particularly preferable.

[formula 6]

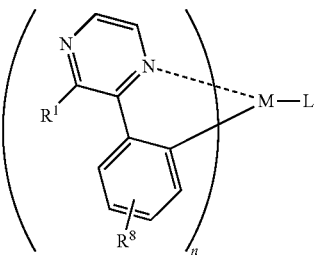

(where wherein $R^1$ is any one selected from the group consisting of hydrogen, a halogen atom, an acyl group, an alkyl group, an alkoxyl group, an aryl group, a cyano group, and a heterocyclic group, $R^8$ is an electron-withdrawing group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

In each of the general formulas (4) to (6), it is preferable that is the ligand L is any one of monoanionic bidentate ligands represented by the following structure formulas (7) to (13) although the ligand L is any ligand of a monoanionic ligand having a β-diketone structure, a monoanionic bidentate ligand having a carboxyl group, and a monoanionic bidentate ligand having a phenolic hydroxyl group. These monoanionic bidentate ligands have higher ability in coordination and are available cheaply, thus, the monoanionic bidentate ligands are effective.

[formula 7]

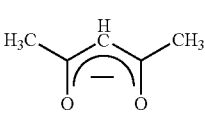

[formula 8]

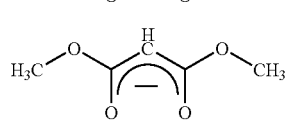

[formula 9]

[formula 10]

[formula 11]

[formula 12]

[formula 13]

In the organometallic complex including the moiety represented by each of the general formulas (1) to (3) or the organometallic complex represented by each of the general formulas (4) to (6), it is preferable that the electron-withdrawing group is any one of a halogeno group and a haloalkyl group, in particular, a fluoro group and a trifluoromethyl group are preferable. These electron-withdrawing groups make it possible to improve the emission quantum efficiency of the organometallic complex including the moiety represented by each of the general formulas (1) to (3) or the organometallic complex represented by each of the general formulas (4) to (6), thus, the monoanionic bidentate ligands effective Also, the inventors have found that an organometallic complex including a moiety represented by the following general formula (14) is a phosphorescent compound in which intersystem crossing to an excited triplet state is likely to occur.

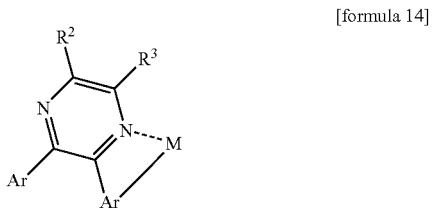

[formula 14]

(where $R^2$ and $R^3$ are individually any one selected from the group consisting of hydrogen, a halogen atom, an acyl group, an alkyl group, an alkoxyl group, an aryl group, a cyano group, and a heterocyclic group, Ar is one of an aryl group and a heterocyclic group, and M is one of an element of Group 9 and an element of Group 10)

Accordingly, the present invention provides an organometallic complex including a moiety represented by the general formula (14). Above all, an organometallic complex represented by the following general formula (15) is particularly preferable.

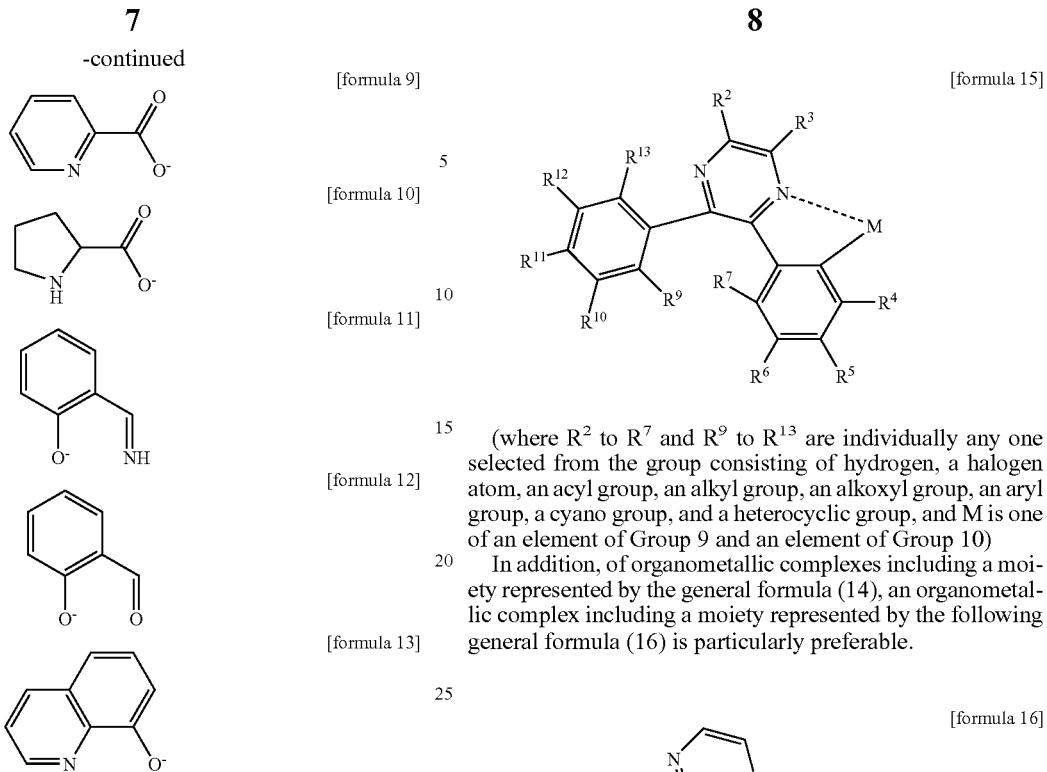

[formula 15]

(where $R^2$ to $R^7$ and $R^9$ to $R^{13}$ are individually any one selected from the group consisting of hydrogen, a halogen atom, an acyl group, an alkyl group, an alkoxyl group, an aryl group, a cyano group, and a heterocyclic group, and M is one of an element of Group 9 and an element of Group 10)

In addition, of organometallic complexes including a moiety represented by the general formula (14), an organometallic complex including a moiety represented by the following general formula (16) is particularly preferable.

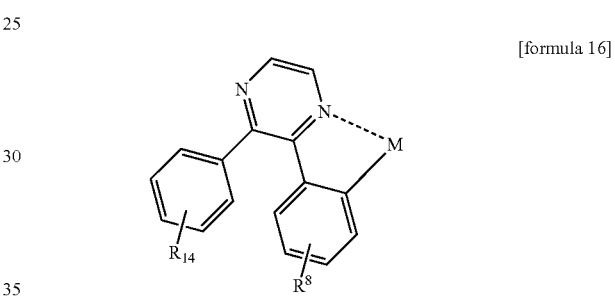

[formula 16]

(where $R^8$ and $R^{14}$ are individually any one selected from the group consisting of hydrogen, a halogen atom, and a holoalkyl group, and M is one of an element of Group 9 and an element of Group 10)

Also, the inventors have found that an organometallic complex represented by the following general formula (17) is a phosphorescent compound in which intersystem crossing to an excited triplet state is likely to occur.

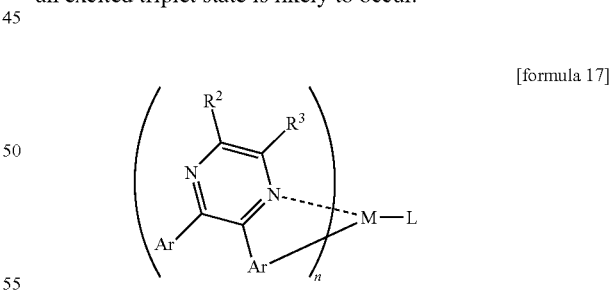

[formula 17]

(where $R^2$ and $R^3$ are individually any one selected from the group consisting of hydrogen, a halogen atom, an acyl group, an alkyl group, an alkoxyl group, an aryl group, a cyano group, and a heterocyclic group, Ar is one of an aryl group and a heterocyclic group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

Accordingly, the present invention provides an organometallic complex represented by the general formula (17). In the general formula (17), it is preferable that is the ligand L is any one of monoanionic bidentate ligands represented by the following structure formulas (7) to (13) although the ligand L is any ligand of a monoanionic ligand having a β-diketone structure, a monoanionic bidentate ligand having a carboxyl group, and a monoanionic bidentate ligand having a phenolic hydroxyl group. These monoanionic ligands have higher ability in coordination and are available cheaply, thus, the monoanionic bidentate ligands are effective.

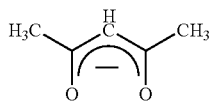
[formula 7]

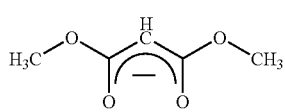
[formula 8]

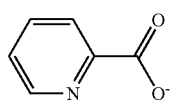
[formula 9]

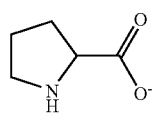
[formula 10]

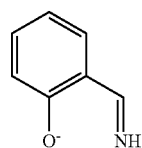
[formula 11]

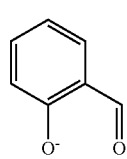
[formula 12]

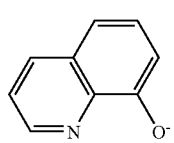
[formula 13]

Also, the inventors have found that an organometallic complex represented by the following general formula (18) is a phosphorescent compound in which intersystem crossing to an excited triplet state is likely to occur.

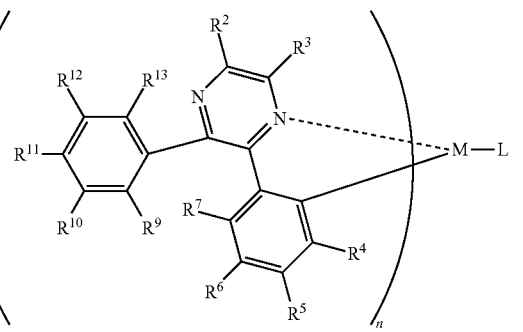
[formula 18]

(where $R^2$ to $R^7$ and $R^9$ to $R^{13}$ are individually any one selected from the group consisting of hydrogen, a halogen atom, an acyl group, an alkyl group, an alkoxyl group, an aryl group, a cyano group, and a heterocyclic group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

In the general formula (18), it is preferable that is the ligand L is any one of monoanionic bidentate ligands represented by the following structure formulas (7) to (13) although the ligand L is any ligand of a monoanionic ligand having a β-diketone structure, a monoanionic bidentate ligand having a carboxyl group, and a monoanionic bidentate ligand having a phenolic hydroxyl group. These monoanionic ligands have higher ability in coordination and are available cheaply, thus, the monoanionic bidentate ligands are effective.

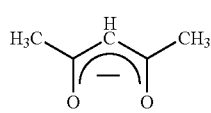
[formula 7]

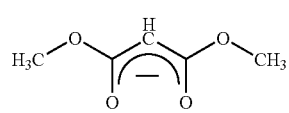
[formula 8]

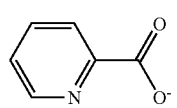
[formula 9]

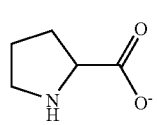
[formula 10]

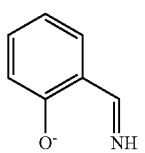
[formula 11]

[formula 12]

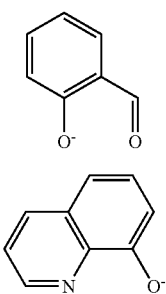

[formula 13]

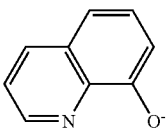

Also, the inventors have found that an organometallic complex represented by the following general formula (19) is a phosphorescent compound in which intersystem crossing to an excited triplet state is likely to occur.

[formula 19]

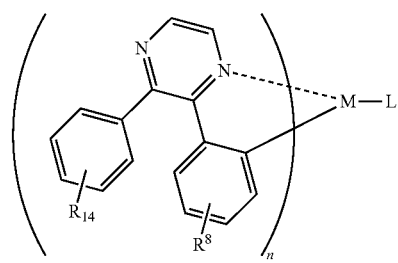

(where $R^8$ and $R^{14}$ are individually any one selected from the group consisting of hydrogen, a halogen atom, and a holoalkyl group, and M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group)

In the general formula (19), it is preferable that is the ligand L is any one of monoanionic bidentate ligands represented by the following structure formulas (7) to (13) although the ligand L is any ligand of a monoanionic ligand having a β-diketone structure, a monoanionic bidentate ligand having a carboxyl group, and a monoanionic bidentate ligand having a phenolic hydroxyl group. These monoanionic ligands have higher ability in coordination and are available cheaply, thus, the monoanionic bidentate ligands are effective.

[formula 7]

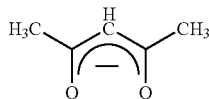

[formula 8]

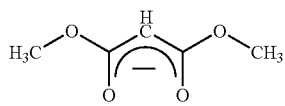

[formula 9]

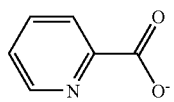

[formula 10]

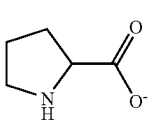

[formula 11]

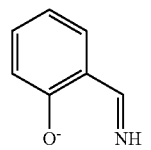

[formula 12]

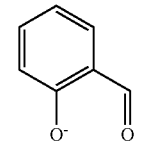

[formula 13]

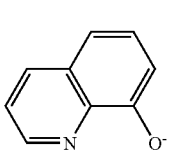

In the organometallic complex including the moiety represented by the general formula (14), the organometallic complex represented by the general formula (17), or the organometallic complex represented by the general formula (17) where the L is any one of the monoanionic bidentate ligands represented by the following structure formulas (7) to (13), it is preferable that (a) at least one of $R^2$ and $R^3$ is an electron-withdrawing group, (b) Ar has an electron-withdrawing group, or (c) at least one of $R^2$ and $R^3$ is an electron-withdrawing group and Ar has an electron-withdrawing group. These electron-withdrawing groups enable the organometallic complex including the moiety represented by the general formula (14), the organometallic complex represented by the general formula (17), or the organometallic complex represented by the general formula (17) where the L is any one of the monoanionic bidentate ligands represented by the following structure formulas (7) to (13) to emit more intense phosphorescence, thus, the monoanionic bidentate ligands are effective.

[formula 7]

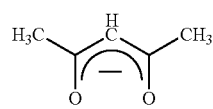

[formula 8]

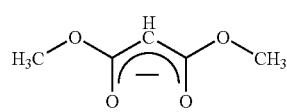

[formula 9]

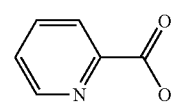

[formula 10]

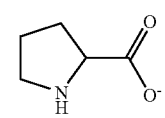

[formula 11]

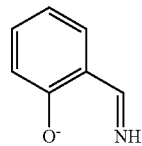

[formula 12]

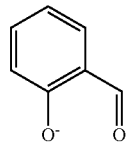

[formula 13]

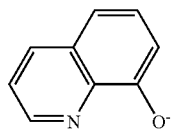

In the organometallic complex including the moiety represented by the general formula (15), the organometallic complex represented by the general formula (18), or the organometallic complex represented by the general formula (18) where the L is any one of the monoanionic bidentate ligands represented by the following structure formulas (7) to (13), it is preferable that at least one of $R^2$ to $R^7$ and $R^9$ to $R^{13}$ is an electron-withdrawing group. This electron-withdrawing group enables the organometallic complex including the moiety represented by the general formula (15), the organometallic complex represented by the general formula (18), or the organometallic complex represented by the general formula (18) where the L is any one of the monoanionic bidentate ligands represented by the following structure formulas (7) to (13) to emit more intense phosphorescence, thus, the monoanionic bidentate ligands are effective.

[formula 7]

[formula 8]

[formula 9]

[formula 10]

[formula 11]

[formula 12]

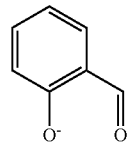

[formula 13]

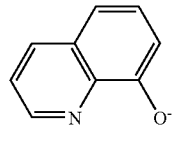

In the organometallic complex including the moiety represented by the general formula (16), the organometallic complex represented by the general formula (19), or the organometallic complex represented by the general formula (19) where the L is any one of the monoanionic bidentate ligands represented by the following structure formulas (7) to (13), it is preferable that at least one of $R^8$ and $R^{14}$ is an electron-withdrawing group. This electron-withdrawing group enables the organometallic complex including the moiety represented by the general formula (16), the organometallic complex represented by the general formula (19), or the organometallic complex represented by the general formula (19) where the L is any one of the monoanionic bidentate ligands represented by the following structure formulas (7) to (13) to emit more intense phosphorescence, thus, the monoanionic bidentate ligands are effective.

[formula 7]

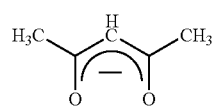

[formula 8]

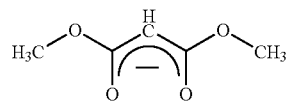

[formula 9]

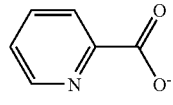

[formula 10]

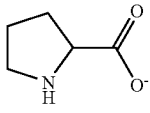

[formula 11]

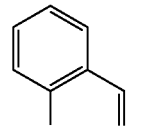

[formula 12]

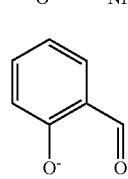

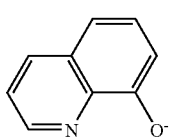

[formula 13]

In the general formulas (14) to (19), it is preferable that the electron-withdrawing group is any one of a halogeno group and a haloalkyl group, in particular, a fluoro group and a trifluoromethyl group are preferable. These electron-withdrawing groups make it possible to improve the emission quantum efficiency of the organometallic complex including the moiety represented by each of the general formulas (14) to (16) or the organometallic complex represented by each of the general formulas (17) to (19), thus, the monoanionic bidentate ligands are effective.

For more efficient phosphorescence, a heavy metal is preferable as the central metal in light of heavy atom effect. Therefore, the present invention has a feature that the central metal M is one of iridium and platinum the general formulas (1) to (6) and (14) to (19).

Now, since the organometallic complex according to the present invention is able to covert triplet excitation energy into luminescence, application of the organometallic complex to a light-emitting element makes it possible to achieve higher efficiency, which is quite effective. Therefore, the present invention also includes a light-emitting element using the organometallic complex according to the present invention.

In this case, the use of the organometallic complex according to the present invention as a light emitter as mentioned in the Non-Patent Reference 5 is more effective in light of the luminous efficiency although the organometallic complex may be used as a sensitizer as mentioned in the Non-Patent Reference 6. Therefore, the present invention is characterized by including a light-emitting element using the organometallic complex according to the present invention as a light emitter.

Since the thus obtained light-emitting element according to the present invention is able to achieve a higher luminous efficiency, a light-emitting device (an image display device or a light-emitting device) using this light-emitting element is able to achieve a lower power consumption. Therefore, the present invention also includes a light-emitting device using the light-emitting element according to the present invention.

The light-emitting device in the specification and the claims indicate an image display device a light-emitting device using a light-emitting element. In addition, the light-emitting device also includes all of a module in which a connecter, for example, an anisotropic conductive film, a TAB (Tape Automated Bonding) tape, or a TCP (Tape Carrier Package), is attached to a light-emitting element, a module in which a printed wiring board is attached to a tip of a TAB tape or a TCP, and a module in which an IC (integrated circuit) is directly mounted on a light-emitting element by a COG (Chip On Glass) method. Further, the light-emitting device includes a light-emitting element to be used for a lighting apparatus and the like.

By implementing the present invention, a novel phosphorescent organometallic complex in which intersystem crossing to an excited triplet state is likely to occur can be provided. In addition, by manufacturing a light-emitting element with the use of the organometallic complex according to the present invention and using the light-emitting element for a light-emitting device, a light-emitting device reduced in power consumption can be provided.

BRIEF DESCRIPTION OF THE DRAWINGS

In the accompanying drawings:

FIG. 9 is a diagram showing an emission spectrum of the light-emitting element using the organometallic complex according to the present invention;

FIG. 10 is a diagram illustrating the structure of a light-emitting element using an organometallic complex according to the present invention;

FIGS. 11A and 11B are diagrams illustrating a light-emitting device;

DETAILED DESCRIPTION OF THE INVENTION

Figure 1:
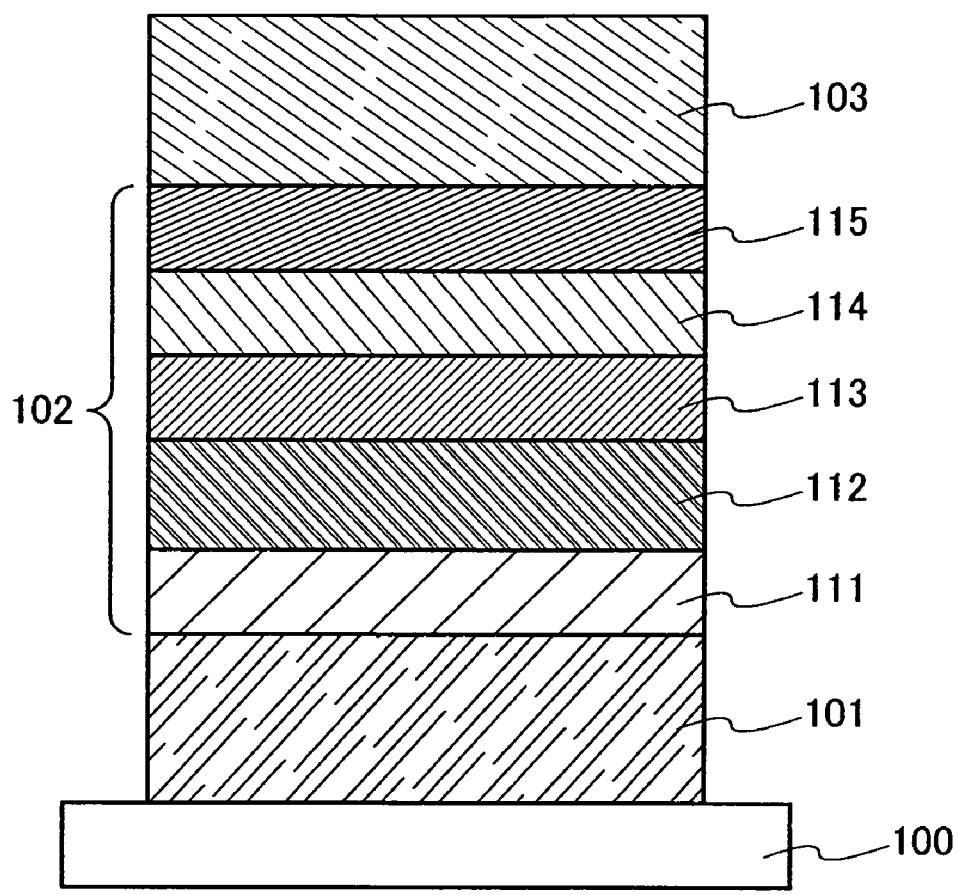
FIG. 1 is a diagram illustrating the structure of a light-emitting element using an organometallic complex according to the present invention.

First, a synthesis method of an organometallic complex according to the present invention will be exemplified below. An organometallic complex according to the present invention (one of the general formulas (1) to (6) and (14) and (19)) can be obtained by orthometallation of a ligand. For example, an organometallic complex that has a ligand represented by the following general formula (20) according to the present invention (that is, the general formula (15) or (18)) is obtained by orthometallation of a ligand represented by the following general formula (20). A method for synthesizing an organometallic complex represented by the general formula (18) according to the present invention with the use of a ligand represented by this general formula (20) will be exemplified below.

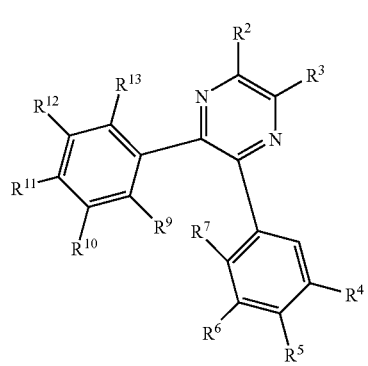

[formula 20]

(where $R^2$ to $R^7$ and $R^9$ to $R^{13}$ are individually any one selected from the group consisting of hydrogen, a halogen atom, an acyl group, an alkyl group, an alkoxyl group, an aryl group, a cyano group, and a heterocyclic group)

It is to be noted that the ligand represented by the general formula (20) can be synthesized by a known method (Japanese Patent Application Laid-Open No. 48-8788), for example, the following synthesis scheme (21). In addition, a ligand represented by the following general formula (22) can also be synthesized in accordance with a similar synthesis scheme. The other ligand in an organometallic complex according to the present invention can also be synthesized in accordance with a similar method.

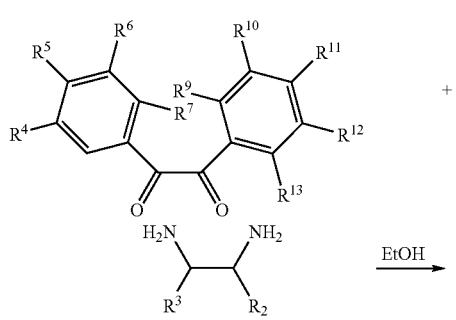

[formula 21]

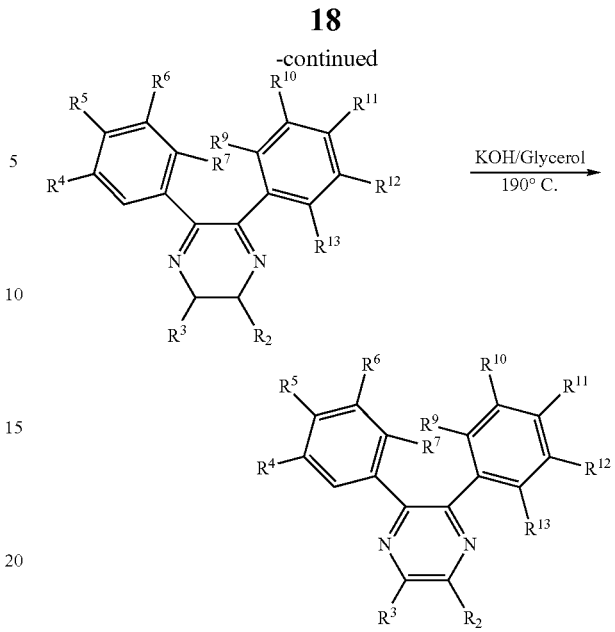

(where $R^2$ to $R^7$ and $R^9$ to $R^{13}$ are individually any one selected from the group consisting of hydrogen, a halogen atom, an acyl group, an alkyl group, an alkoxyl group, an aryl group, a cyano group, and a heterocyclic group)

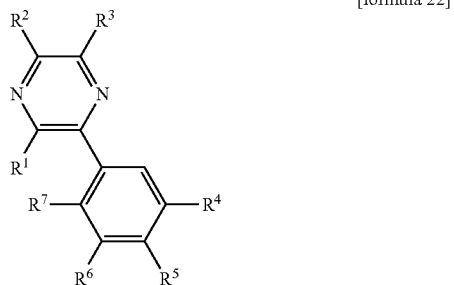

[formula 22]

(where $R^1$ to $R^3$ are individually any one selected from the group consisting of hydrogen, a halogen atom, an acyl group, an alkyl group, an alkoxyl group, an aryl group, a cyano group, and a heterocyclic group, any one (at least one) of $R^4$ to $R^7$ is an electron-withdrawing group, the others of $R^4$ to $R^7$ are individually any one selected form the group consisting of hydrogen, a halogen atom, an acyl group, an alkyl group, an alkoxyl group, an aryl group, a cyano group, and a heterocyclic group)

With the use of the thus obtained ligand represented by the general formula (20), an orthometalated complex that is an organometallic complex according to the present invention is formed. For orthometallation in this case, a known synthesis method may be used.

For example, when an organometallic complex according to the present invention with iridium as a central metal is synthesized, a chloro-bridged dimer complex is first synthesized with the use of iridium chloride hydrate as a raw material for the central metal by mixing the iridium chloride hydrate with the ligand represented by the general formula (20) and holding the iridium chloride hydrate mixed with the ligand at reflux in a nitrogen atmosphere (the following synthesis scheme (23)). Next, by mixing the obtained dinuclear complex with a ligand L and holding the nuclear complex mixed with the ligand L at reflux in a nitrogen atmosphere, the chlorine bridge is cut with the ligand L to obtain an organometallic complex according to the present invention (the following synthesis scheme (24)).

[formula 23]

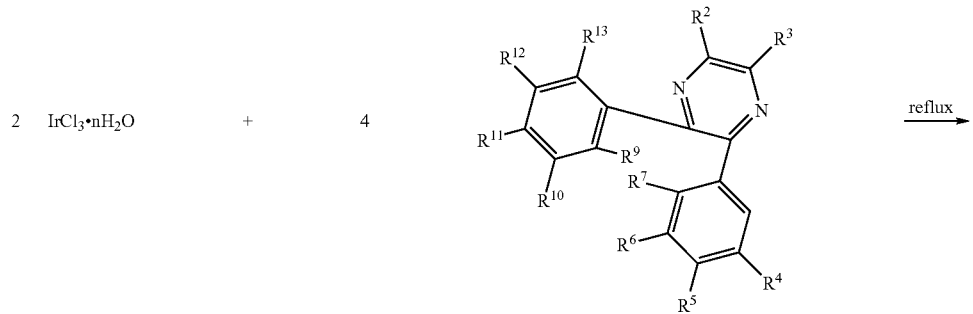

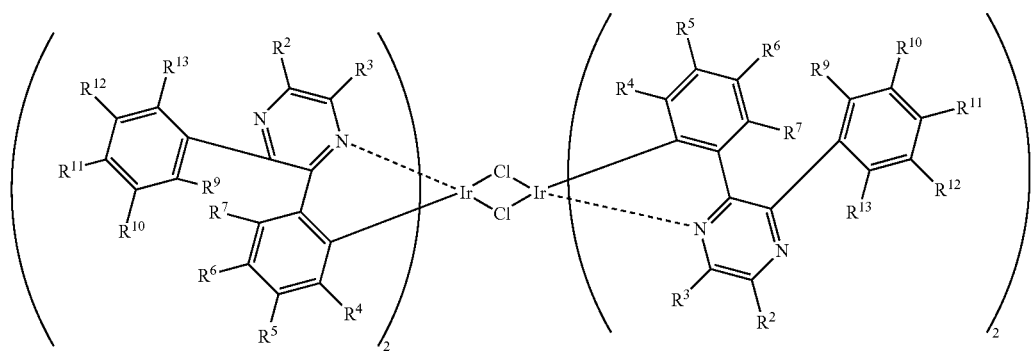

(where R² to R⁷ and R⁹ to R¹³ are individually any one selected from the group consisting of hydrogen, a halogen atom, an acyl group, an alkyl group, an alkoxyl group, an aryl group, a cyano group, and a heterocyclic group)

(where R² to R⁷ and R⁹ to R¹³ are individually any one selected from the group consisting of hydrogen, a halogen atom, an acyl group, an alkyl group, an alkoxyl group, an aryl group, a cyano group, and a heterocyclic group, and L is any

[formula 24]

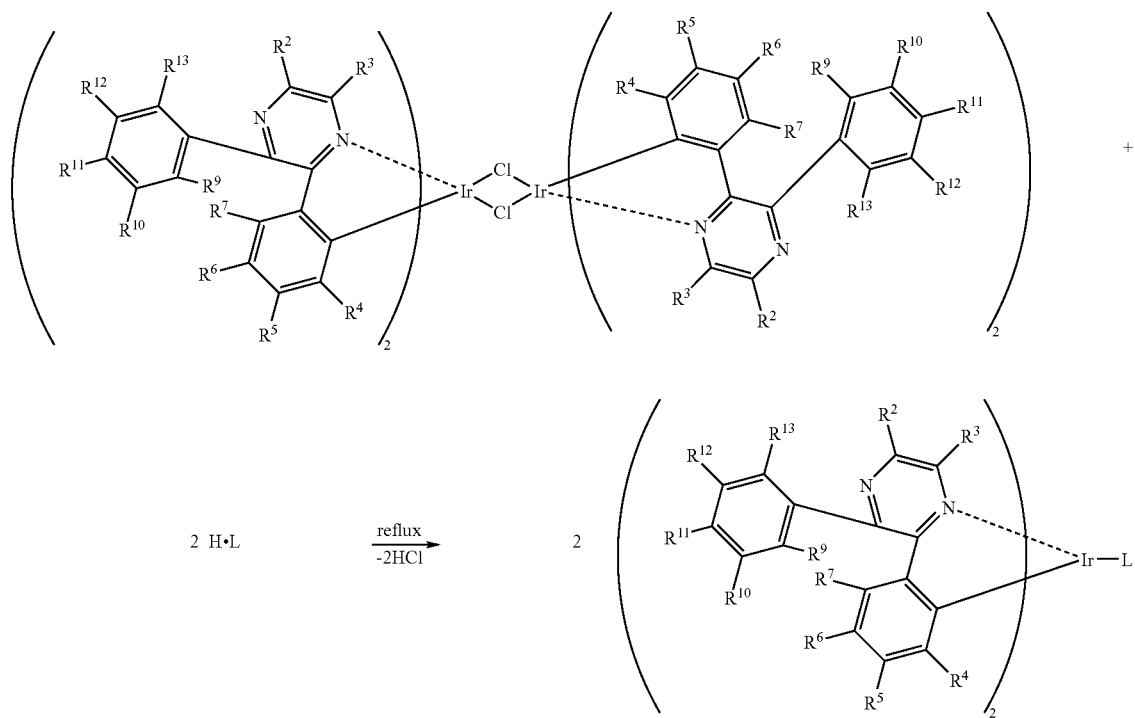

one of a monoanionic ligand having a β-diketone structure, a monoanionic bidentate ligand having a carboxyl group, and a monoanionic bidentate ligand having a phenolic hydroxyl group)

The method to be used for synthesizing an organometallic complex is not to be considered limited to the synthesis method described above.

Since the thus obtained organometallic complex according to the present invention has the electron transporting pyrazine derivative as a ligand, the organometallic complex has a carrier transporting property, and can be used for electronic devices. In addition, organometallic complexes that have properties such as various luminescent colors can be obtained by changing the structure of the ligand represented by the general formula (20). Specific examples thereof include, for example, compounds (25) to (105) shown in the following Tables 1 to 9. In the tables, each L is indicated by a number for the structure formula (corresponding to the previously cited number for the structure formula). However, organometallic complexes to be used in the present invention is not considered limited to those shown in the following tables.

TABLE 1

| structural formula | general formula | $R^1$ | $R^2$ | $R^3$ | Ar | M | L |
|---|---|---|---|---|---|---|---|
| (25) | (4) | —H | —H | —H | 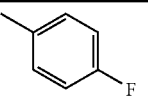 | Ir | (7) |
| (26) | (4) | —CH$_3$ | —H | —H | 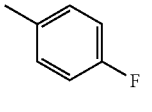 | Ir | (7) |
| (27) | (4) | —H | —CN | —CN | 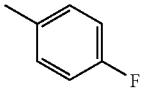 | Ir | (7) |

TABLE 1-continued

| structural formula | general formula | $R^1$ | $R^2$ | $R^3$ | Ar | M | L |
|---|---|---|---|---|---|---|---|
| (28) | (4) | —CH$_3$ | —CN | —CN | 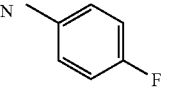 | Ir | (7) |
| (29) | (4) | —H | —H | —H | 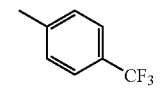 | Ir | (7) |
| (30) | (4) | —CH$_3$ | —H | —H | 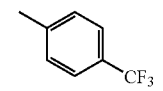 | Ir | (7) |
| (31) | (4) | —H | —CN | —CN | 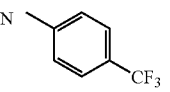 | Ir | (7) |
| (32) | (4) | —CH$_3$ | —CN | —CN | 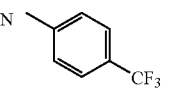 | Ir | (7) |
| (33) | (4) | —H | —H | —H | 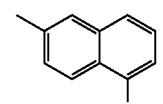 | Ir | (7) |
| (34) | (4) | —CH$_3$ | —H | —H | 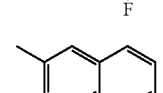 | Ir | (7) |
| (35) | (4) | —H | —CN | —CN | 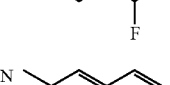 | Ir | (7) |

TABLE 2

| structural formula | general formula | $R^1$ | $R^2$ | $R^3$ | Ar | M | L |
|---|---|---|---|---|---|---|---|
| (36) | (4) | —CH$_3$ | —CN | —CN | 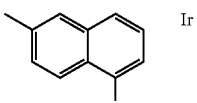 | Ir | (7) |
| (37) | (4) | —CH$_3$ | —H | —H | 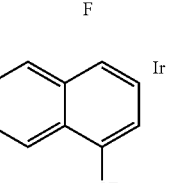 | Ir | (7) |
| (38) | (4) | —H | —H | —H | 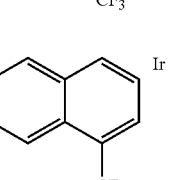 | Ir | (7) |

TABLE 2-continued
| structural formula | general formula | R¹ | R² | R³ | Ar | M | L |
|---|---|---|---|---|---|---|---|
| (39) | (4) | —CH₃ | —H | —H | 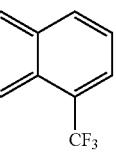 | Ir | (7) |
| (40) | (4) | —H | —CN | —CN | 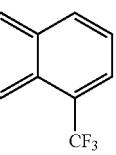 | Ir | (7) |
| (41) | (4) | —CH₃ | —CN | —CN | 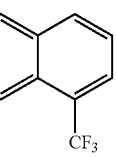 | Ir | (7) |
| (42) | (4) | —H | 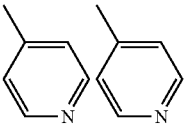 | 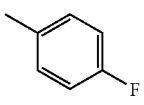 | 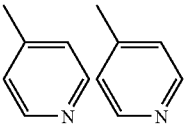 | Ir | (7) |
| (43) | (4) | —CH₃ | 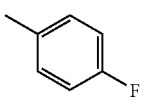 | 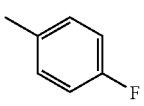 | 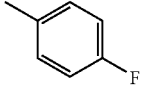 | Ir | (7) |
| (44) | (4) | —H | —H | —H | 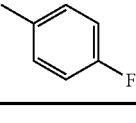 | Ir | (8) |
| (45) | (4) | H | H | H | 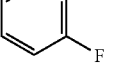 | Ir | (9) |
| (46) | (4) | —H | —H | —H | 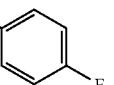 | Ir | (10) |
TABLE 3
| structural formula | general formula | R¹ | R² | R³ | Ar | M | L |
|---|---|---|---|---|---|---|---|
| (47) | (4) | —H | —H | —H | 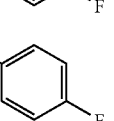 | Ir | (11) |
| (48) | (4) | —H | —H | —H | | Ir | (12) |
| (49) | (4) | —H | —H | —H | | Ir | (13) |

TABLE 4

| structural formula | general formula | R¹ | R² | R³ | R⁴ | R⁵ | R⁶ | R⁷ | M | L |
|---|---|---|---|---|---|---|---|---|---|---|
| (50) | (2) | —H | —H | —H | —F | —CH₃ | —H | —H | Ir | (7) |
| (51) | (2) | —H | —H | —H | —CF₃ | —CH₃ | —H | —H | Ir | (7) |
| (52) | (2) | —H | —H | —H | —F | —C(=O)CH₃ | —H | —H | Ir | (7) |
| (53) | (2) | —H | —H | —H | —CF₃ | —C(=O)CH₃ | —H | —H | Ir | (7) |
| (54) | (2) | —H | —H | —H | —F | —OCH₃ | —H | —H | Ir | (7) |
| (55) | (2) | —H | —H | —H | —CF₃ | —OCH₃ | —H | —H | Ir | (7) |
| (56) | (2) | —H | —CN | —CN | —F | —CH₃ | —H | —H | Ir | (7) |
| (57) | (2) | —H | —CN | —CN | —CF₃ | —CH₃ | —H | —H | Ir | (7) |
| (58) | (2) | —H | —CN | —CN | —F | —C(=O)CH₃ | —H | —H | Ir | (7) |
| (59) | (2) | —H | —CN | —CN | —CF₃ | —C(=O)CH₃ | —H | —H | Ir | (7) |
| (60) | (2) | —H | —CN | —CN | —F | —OCH₃ | —H | —H | Ir | (7) |
| (61) | (2) | —H | —CN | —CN | —CF₃ | —OCH₃ | —H | —H | Ir | (7) |
| (62) | (2) | —H | 4-pyridyl | 4-pyridyl | —F | —CH₃ | —H | —H | Ir | (7) |
| (63) | (2) | —H | 4-pyridyl | 4-pyridyl | —CF₃ | —CH₃ | —H | —H | Ir | (7) |
| (64) | (2) | —H | —H | —H | —F | —CH₃ | —H | —H | Ir | (8) |

TABLE 5

| structural formula | general formula | R¹ | R² | R³ | R⁴ | R⁵ | R⁶ | R⁷ | M | L |
|---|---|---|---|---|---|---|---|---|---|---|
| (65) | (2) | —H | —H | —H | —F | —CH₃ | —H | —H | Ir | (9) |
| (66) | (2) | —H | —H | —H | —F | —CH₃ | —H | —H | Ir | (10) |
| (67) | (2) | —H | —H | —H | —F | —CH₃ | —H | —H | Ir | (11) |
| (68) | (2) | —H | —H | —H | —F | —CH₃ | —H | —H | Ir | (12) |
| (69) | (2) | —H | —H | —H | —F | —CH₃ | —H | —H | Ir | (13) |

TABLE 6

| structural formula | general formula | R² | R³ | Ar | M | L |
|---|---|---|---|---|---|---|
| (70) | (17) | —H | —H | 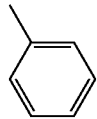 | Ir | (7) |
| (71) | (17) | —CN | —CN | 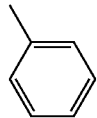 | Ir | (7) |
| (72) | (17) | 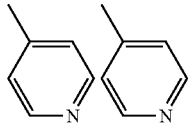 | 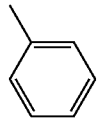 |  | Ir | (7) |
| (73) | (17) | —H | —H |  | Ir | (7) |
| (74) | (17) | —CN | —CN |  | Ir | (7) |
| (75) | (17) | 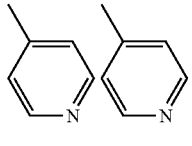 | 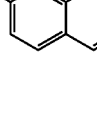 |  | Ir | (7) |
| (76) | (17) | —H | —H |  | Ir | (8) |
| (77) | (17) | —H | —H | 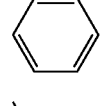 | Ir | (9) |
| (78) | (17) | —H | —H | 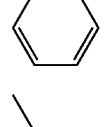 | Ir | (10) |
| (79) | (17) | —H | —H | 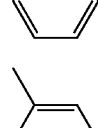 | Ir | (11) |
| (80) | (17) | —H | —H | 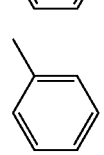 | Ir | (12) |
| (81) | (17) | —H | —H | 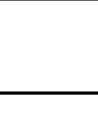 | Ir | (13) |

TABLE 7

| structural formula | general formula | $R^2$ | $R^3$ | $R^4$ | $R^5$ | $R^6$ | $R^7$ | $R^9$ | $R^{10}$ | $R^{11}$ | $R^{12}$ | $R^{13}$ | M | L |
|---|---|---|---|---|---|---|---|---|---|---|---|---|---|---|
| (82) | (18) | —H | —H | —F | —$CH_3$ | —H | —H | —H | —F | —$CH_3$ | —H | —H | Ir | (7) |
| (83) | (18) | —H | —H | —$CF_3$ | —$CH_3$ | —H | —H | —H | —$CF_3$ | —$CH_3$ | —H | —H | Ir | (7) |
| (84) | (18) | —H | —H | —F | 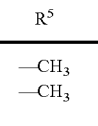 | —H | —H | —H | —F | 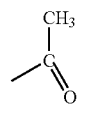 | —H | —H | Ir | (7) |
| (85) | (18) | —H | —H | —$CF_3$ | 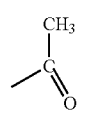 | —H | —H | —H | —$CF_3$ | 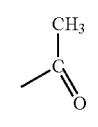 | —H | —H | Ir | (7) |
| (86) | (18) | —H | —H | —F | —$OCH_3$ | —H | —H | —H | —F | —$OCH_3$ | —H | —H | Ir | (7) |
| (87) | (18) | —H | —H | —$CF_3$ | —$OCH_3$ | —H | —H | —H | —$CF_3$ | —$OCH_3$ | —H | —H | Ir | (7) |
| (88) | (18) | —CN | —CN | —F | —$CH_3$ | —H | —H | —H | —F | —$CH_3$ | —H | —H | Ir | (7) |
| (89) | (18) | —CN | —CN | —$CF_3$ | —$CH_3$ | —H | —H | —H | —$CF_3$ | —$CH_3$ | —H | —H | Ir | (7) |
| (90) | (18) | —CN | —CN | —F | 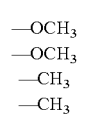 | —H | —H | —H | —F | 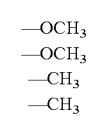 | —H | —H | Ir | (7) |

TABLE 7-continued

| structural formula | general formula | R² | R³ | R⁴ | R⁵ | R⁶ | R⁷ | R⁹ | R¹⁰ | R¹¹ | R¹² | R¹³ | M | L |
|---|---|---|---|---|---|---|---|---|---|---|---|---|---|---|
| (91) | (18) | —CN | —CN | —CF₃ | 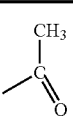 | —H | —H | —H | —CF₃ | 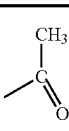 | —H | —H | Ir | (7) |
| (92) | (18) | —CN | —CN | —F | —OCH₃ | —H | —H | —H | —F | —OCH3 | —H | —H | Ir | (7) |
| (93) | (18) | —CN | —CN | —CF₃ | —OCH3 | —H | —H | —H | —CF₃ | —OCH₃ | —H | —H | Ir | (7) |

TABLE 8

| structural formula | general formula | R² | R³ | R⁴ | R⁵ | R⁶ | R⁷ | R⁹ | R¹⁰ | R¹¹ | R¹² | R¹³ | M | L |
|---|---|---|---|---|---|---|---|---|---|---|---|---|---|---|
| (94) | (18) | 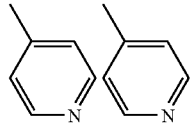 | 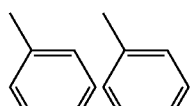 | —F | CH3 | —H | —H | —H | —F | —CH₃ | —H | —H | Ir | (7) |
| (95) | (18) | 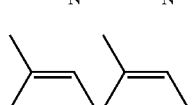 | 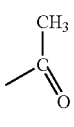 | —CF₃ | —CH₃ | —H | —H | —H | —CF₃ | —CH₃ | —H | —H | Ir | (7) |
| (96) | (18) | 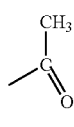 | 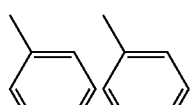 | —F | 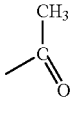 | —H | —H | —H | —F | 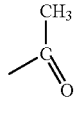 | —H | —H | Ir | (7) |
| (97) | (18) | 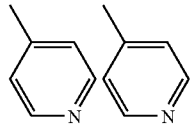 |  | —CF₃ | CH₃-C(=O)- | —H | —H | —H | —CF₃ | CH₃-C(=O)- | —H | —H | Ir | (7) |
| (98) | (18) | (pyridyl) | (pyridyl) | —F | —OCH₃ | —H | —H | —H | —F | —OCH₃ | —H | —H | Ir | (7) |
| (99) | (18) | (pyridyl) | (pyridyl) | —CF₃ | —OCH₃ | —H | —H | —H | —CF₃ | —OCH₃ | —H | —H | Ir | (7) |
| (100) | (18) | —H | —H | —F | —CH₃ | —H | —H | —H | —F | —CH₃ | —H | —H | Ir | (8) |
| (101) | (18) | —H | —H | —F | —CH₃ | —H | —H | —H | —F | —CH₃ | —H | —H | Ir | (9) |

TABLE 9

| structural formula | general formula | R² | R³ | R⁴ | R⁵ | R⁶ | R⁷ | R⁹ | R¹⁰ | R¹¹ | R¹² | R¹³ | M | L |
|---|---|---|---|---|---|---|---|---|---|---|---|---|---|---|
| (102) | (18) | —H | —H | —F | —CH₃ | —H | —H | —H | —F | —CH₃ | —H | —H | Ir | (10) |
| (103) | (18) | —H | —H | —F | —CH₃ | —H | —H | —H | —F | —CH₃ | —H | —H | Ir | (11) |
| (104) | (18) | —H | —H | —F | —CH₃ | —H | —H | —H | —F | —CH₃ | —H | —H | Ir | (12) |
| (105) | (18) | —H | —H | —F | —CH₃ | —H | —H | —H | —F | —CH₃ | —H | —H | Ir | (13) |

An organometallic complex according to the present invention can be used as a photosensitizer or a luminescent material. An example of applying an organometallic complex according to the present invention to a light-emitting element will be described below.

A light-emitting element according to the present invention basically has a structure in which a layer including a luminescent material (such as a hole injecting layer, a hole transporting layer, a light-emitting layer, a hole blocking layer, an electron transporting layer, and an electron injecting layer) including the above-described organometallic complex according to the present invention (an organometallic complex including a moiety represented by one of the general formula (1) to (3) and (14) to (16), or an organometallic complex represented by one of the general formula (4) to (6) and (17) to (19)) is sandwiched between a pair of electrodes (an anode and a cathode).

In addition, as materials to be used for the layer including the luminescent material other than the organometallic complex according to the present invention, known materials can be used, and low molecular weight materials and polymer materials can be both used. It is to be noted that the materials for forming the layer may be not only organic compounds but also inorganic materials to be included in a portion of the layer.

Embodiments of light-emitting elements according to the present invention will be described in more detail below.

Embodiment 1

In Embodiment 1, the structure of a light-emitting element that has a hole injecting layer composed of a low molecular weight material, a hole transporting layer, a hole blocking layer, and an electron transporting layer will be described with reference to FIG. 1.

FIG. 1 shows a structure in which a first electrode 101 is formed over a substrate 100, a layer 102 including a luminescent material is formed on the first electrode 101, and a second electrode 103 is formed thereon.

As a material to be used for the substrate 101 here, a material that is used for a conventional light-emitting element may be used. For example, glass, quartz, transparent plastic, and a flexible substrate can be used.

In addition, the first electrode 101 and the second electrode 103 in Embodiment 1 function as an anode and a cathode, respectively.

Namely, the first electrode 101 is formed by using an anode material. As the anode material that can be used here, it is preferable to use a metal, an alloy, an electrically conductive compound, or a mixture thereof, which has a larger work function (a work function of 4.0 eV or more). As specific examples of the anode material, a metal such as gold (Au), platinum (Pt), nickel (Ni), tungsten (W), chromium (Cr), molybdenum (Mo), iron (Fe), cobalt (Co), copper (Cu), or palladium (Pd), and a nitride of a metal material such as TiN can be used in addition to indium tin oxide, indium tin oxide containing silicon oxide, indium zinc oxide of indium oxide mixed with zinc oxide (ZnO) at 2 to 20%, and zinc gallium oxide of zinc oxide mixed with gallium oxide ($Ga_2O_3$) at several %.

On the other hand, as a cathode material to be used for the second electrode 103, it is preferable to use a metal, an alloy, an electrically conductive compound, or a mixture thereof, which has a smaller work function (a work function of 3.8 eV or less). As specific examples of the cathode material, in addition to an element belonging to Group 1 or 2 of the periodic table of the elements, that is, alkali metals such as Li and Cs and alkali-earth metals such as Mg, Ca, and Sr, and an alloy (Mg:Ag or Al:Li) and a compound (LiF, CsF, or $CaF_2$) including the element, a transition metal including a rare-earth metal can be used to form the second electrode 103. The second electrode 103 can be formed also by using a lamination layer of the material mentioned above and a metal (including an alloy) such as Al, Ag, or ITO.

A thin film composed of the above-mentioned anode material and a thin film composed of the above-mentioned cathode material are formed by a method such as evaporation or sputtering to form the first electrode 101 and the second electrode 103, respectively, which preferably have a film thickness of 10 to 500 nm. Finally, a protective layer (a barrier layer) composed of an inorganic material such as SiN or an organic material such as poly(tetrafluoroethylene) or a styrene polymer is formed. The barrier layer may be transparent or non-transparent, and the inorganic material or organic material is formed by a method such as evaporation or sputtering.

Further, in order to protect the organic layer and electrodes of the light-emitting element from oxidation and moisture, a drying agent such as SrOx or SiOx is formed by a method such as electron beam irradiation, evaporation, sputtering, or sol-gel.

In the light-emitting element according to the present invention, light generated by recombination of carriers in the layer including the luminescent material is emitted from one or both of the first electrode 101 and the second electrode 103 to the outside. Namely, the first electrode 101 is formed by using a light-transmitting material when the light is emitted from the first electrode 101 while the second electrode 103 is formed by using a light-transmitting material when the light is emitted from the second electrode 103.

The layer 102 including the luminescent material is formed by stacking a plurality of layers, in Embodiment 1, by stacking a hole injecting layer 111, a hole transporting layer 112, a light-emitting layer 113, a hole blocking layer 114, and an electron transporting layer 115.

As a hole injecting material forming the hole injecting layer 111, phthalocyanine compounds are efficient. For example, phthalocyanine (abbreviation: $H_2$-Pc) and copper phthalocyanine (abbreviation: Cu-Pc) can be used. In addition, 4,4'-bis [N-(4-(N,N-di-m-tolylamino)phenyl)-N-phenylamino]biphenyl (abbreviation: DNTPD) and the like can also be used.

As a hole transporting material forming the hole transporting layer 112, aromatic amine compounds (namely, compounds that have a benzene ring-nitrogen bond) are preferred. Materials that are widely used include, for example, in addition to 4,4'-bis [N-(3-methylphenyl)-N-phenyl-amino]-biphenyl (abbreviation: TPD), derivatives thereof such as 4,4'-bis [N-(1-naphthyl)-N-phenyl-amino]-biphenyl (abbreviation: α-NPD) and starburst aromatic amine compounds such as 4,4',4''-tris (N,N-diphenyl-amino)-triphenylamine (abbreviation: TDATA) and 4,4',4''-tris [N-(3-methylphenyl)-N-phenyl-amino]-triphenylamine (abbreviation: MTDATA) and so on. In addition, a composite material of a conductive inorganic material and the organic material mentioned above can be also used.

The light-emitting layer 113 includes an organometallic complex that has any one of the general formulas (1) to (3) and (14) to (16) as a moiety or an organometallic complex represented by any one of the general formulas (4) to (6) and (17) to (19), and is formed by co-evaporation of this organometallic complex and a host material. As the host material, known materials can be used, which include the above-mentioned hole transporting materials and electron transporting materials to be described in addition to triphenylaminoquinoxaline (abbreviation: TPAQn), 4,4'-bis (N-carbazolyl)-biphenyl (abbreviation: CBP), and 2,2',2''-(1,3,5-benzenetri-yl) tris-[1-phenyl-1H-benzimidazole] (abbreviation: TPBI).

As a hole blocking material forming the hole blocking layer 114, bis (2-methyl-8-quinolinolato)-4-phenylphenolato-aluminum (abbreviation: BAlq), 1,3-bis [5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and the like can be used.

As an electron transporting material forming the electron transporting layer 115, metal complexes that have a quinoline skeleton or a benzoquinoline skeleton such as tris (8-quinolinolato)aluminum (abbreviation: $Alq_3$), tris (4-methyl-8-quinolinolato)aluminum (abbreviation: $Almq_3$), and bis (10-hydroxybenzo [h]-quinolinato)beryllium (abbreviation: $BeBq_2$), and the above-mentioned BAlq are preferred. In addition, there are also metal complexes that have an oxazole or thiazole ligand such as bis [2-(2-hydroxyphenyl)-benzoxazolato]zinc (abbreviation: $Zn(BOX)_2$) and bis [2-(2-hydroxyphenyl)-benzothiazolato]zinc (abbreviation: $Zn(BTZ)_2$). Further, in addition to metal complexes, 2-(4-biphenylyl)-5-(4-tert-butylphenyl)-1,3,4-oxadiazole (abbreviation: PBD), the above-mentioned OXD-7, TAZ, p-EtTAZ, BPhen, and BCP, and the like can also be used as the electron transporting material. Moreover, inorganic materials such as TiOx can also be used.

Thus, a light-emitting element that has the light-emitting layer 113 including the organometallic complex according to the present invention, the hole injecting layer 111 composed of a low molecular weight material, the hole transporting layer 112, the hole blocking layer 114, and the electron transporting layer 115 can be formed.

It is to be noted that in Embodiment 1, the organometallic complex according to the present invention is used as a guest material in the light-emitting layer 113 to be a light-emitting element in which luminescence obtained from the organometallic complex according to the present invention is a luminescent color.

Embodiment 2

Figure 2:
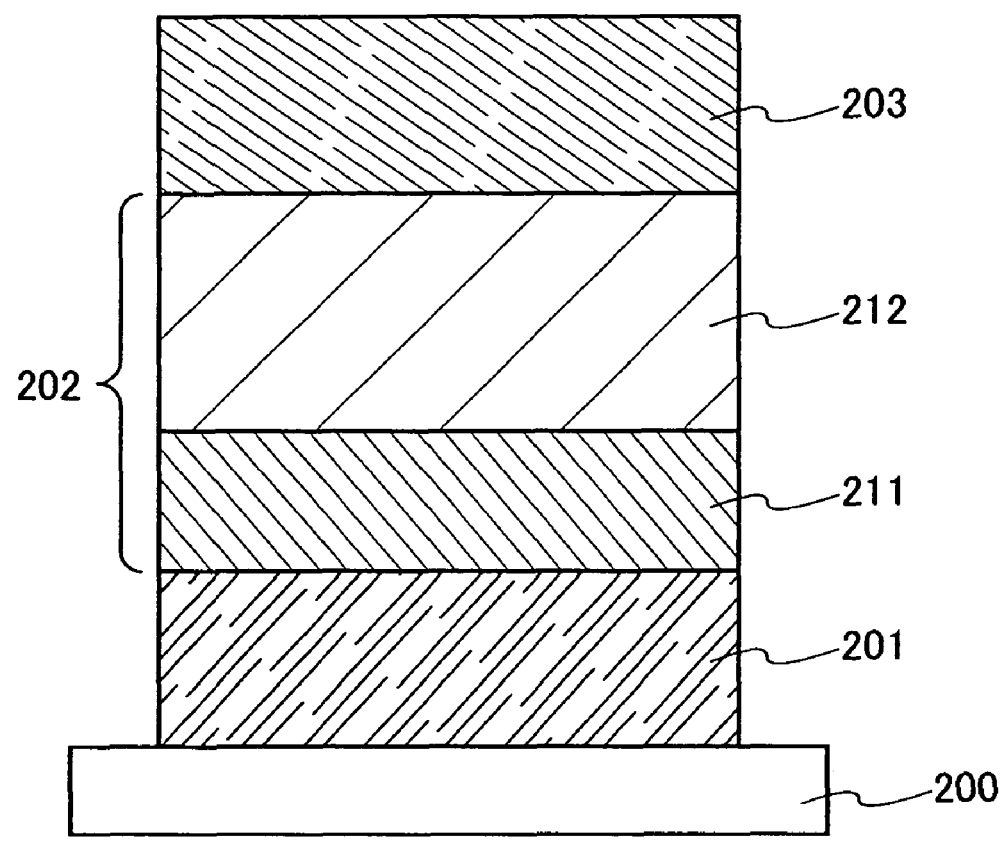
FIG. 2 is a diagram illustrating the structure of a light-emitting element using an organometallic complex according to the present invention.

In Embodiment 2, the structure of a light-emitting element that has a light-emitting layer including an organometallic complex according to the present invention and a hole injecting layer composed of a polymer material, which are formed by a wet process, will be described with reference to FIG. 2.

Since a substrate 200, a first electrode 201, and a second electrode 203 can be formed in the same way with the use of the same materials as those in Embodiment Mode 1, descriptions thereof are omitted.

In addition, a layer 202 including a luminescent material is formed by stacking a plurality of layers, in Embodiment 2, formed by stacking a hole injecting layer 211 and a light-emitting layer 212.

As a hole injecting material forming the hole injection layer, polyethylene dioxythiophene (abbreviation: PEDOT) doped with polystyrene sulfonate (abbreviation: PSS), polyaniline, polyvinyl carbazole (abbreviation: PVK), and the like can be used.

The light-emitting layer 212 includes as a guest material an organometallic complex that has any one of the general formulas (1) to (3) and (14) to (16) as a moiety or an organometallic complex represented by any one of the general formulas (4) to (6) and (17) to (19). As a host material, any bipolar materials may be used, or a hole transporting material and an electron transporting material may be mixed to be bipolar. Here, first, a hole transporting polymer compound (for example, PVK) and the above-mentioned electron transporting material (for example, PBD) are dissolved in the same solvent at 7:3 (molar ratio), and an appropriate amount of the organometallic complex according to the present invention (approximately 5 wt %) is further added to prepare a solution. The light-emitting layer 212 can be obtained by wet application of this solution.

Thus, a light-emitting element that has the light-emitting layer 212 including the organometallic complex according to the present invention and the hole injecting layer 211 composed of a polymer material, which are formed by a wet process, can be obtained.

Embodiment 3

Figure 3:
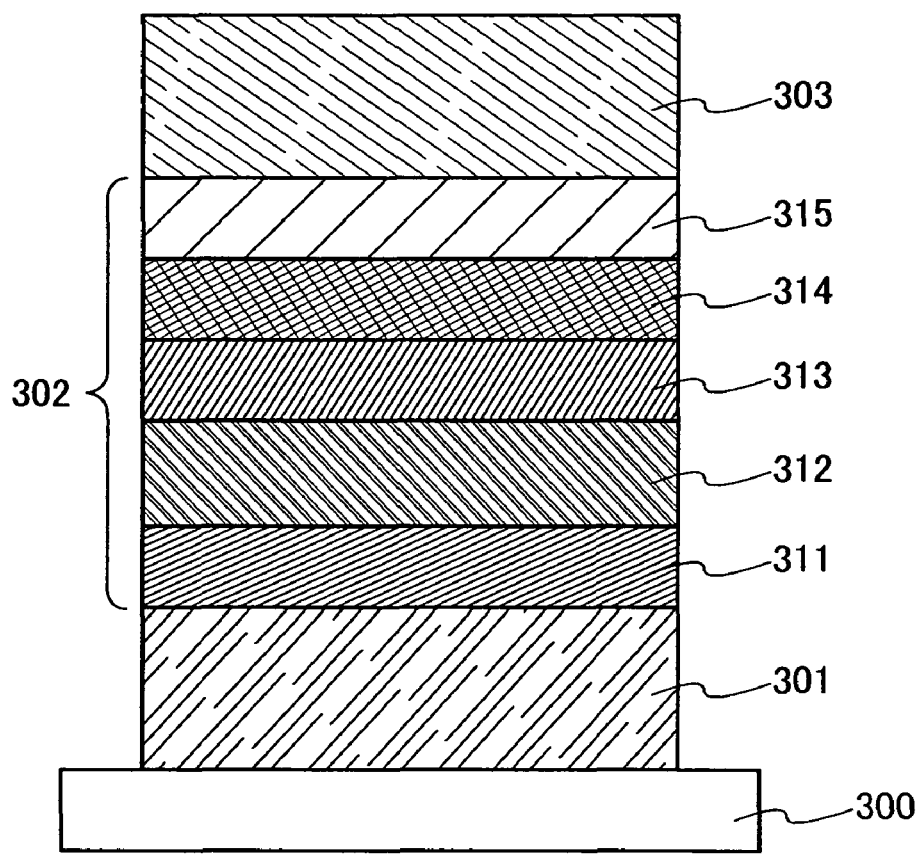
FIG. 3 is a diagram illustrating the structure of a light-emitting element using an organometallic complex according to the present invention.

In Embodiment 3, the structure of a light-emitting element that has a light-emitting layer including two of an organometallic complex according to the present invention and a fluorescent compound, a hole injecting layer composed of a low molecular weight material, a hole transporting layer, a hole blocking layer, and an electron transporting layer will be described with reference to FIG. 3.

Since a substrate 300, a first electrode 301, a second electrode 303, a hole injecting layer 311, a hole transporting layer 312, a hole blocking layer 314, and an electron transporting layer 315 can be formed in the same way with the use of the same materials as those in Embodiment Mode 1, descriptions thereof are omitted.

A light-emitting layer 313 in the present embodiment is composed of a host material, an organometallic complex according to the present invention, which is a first guest material, and a fluorescent compound, which is a second guest material. As the host material, the materials mentioned in Embodiment 1 may be used.

Further, as the second guest material, known fluorescent compounds can be used, and specifically, DCM1, DCM2, DCJTB, quinacridone, N,N-dimethylquinacridone, rubrene, perylene, DPT, Co-6, PMDFB, BTX, ABTX, and the like can be used.

In Embodiment 3, as in the case of Non-Patent Reference 6, the organometallic complex according to the present invention, which is the first guest material, acts as a sensitizer in the light-emitting layer 313 to increase the number of excited singlet states of the fluorescent compound, which is the second guest material. Therefore, the light-emitting element in Embodiment 3 is a light-emitting element that produces luminescence obtained from the fluorescent material as a luminescent color, and the luminous efficiency of the fluorescent compound can be improved more than ever before. It is to be noted that either one of an anode and a cathode may be laminated first in the light-emitting element using the organometallic complex according to the present invention.

Figure 4A:
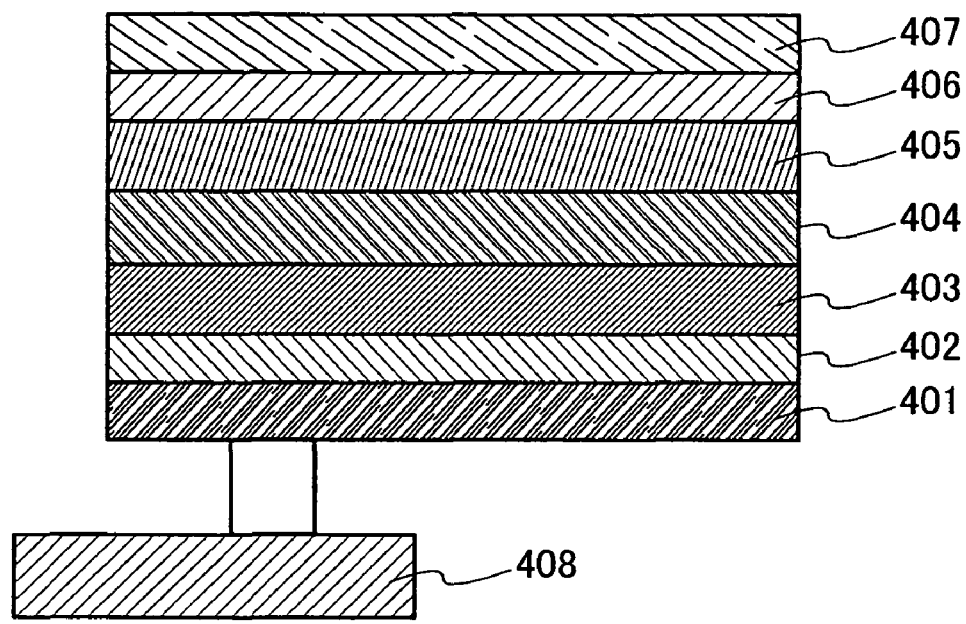
FIGS. 4A and 4B are diagrams illustrating the structures of light-emitting elements according to the present invention.
Figure 4B:
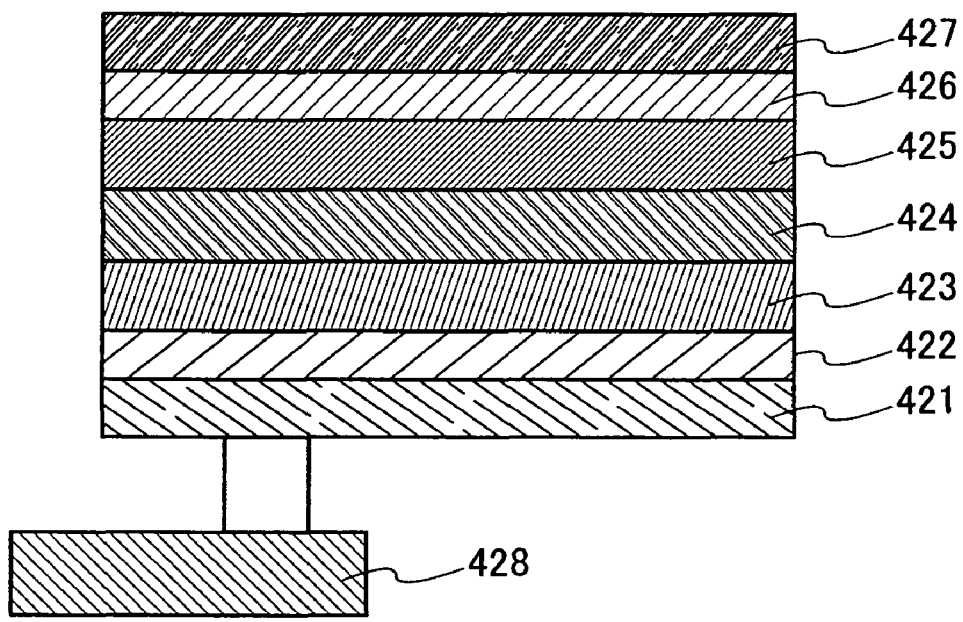

For example, FIG. 4A is a diagram in which an anode for a light-emitting element is laminated first, and FIG. 4B is a diagram in which a cathode for a light-emitting element is laminated first. In FIG. 4A, an anode 401, a hole injecting layer 402, a hole transporting layer 403, a light-emitting layer 404, an electron transporting layer 405, an electron injecting layer 406, and a cathode 407 are stacked in this order. In this case, a p-channel TFr 408 is fixed to the anode 401. In addition, in FIG. 4B, a cathode 421, an electron injecting layer 422, an electron transporting layer 423, a light-emitting layer 424, a hole transporting layer 425, a hole injecting layer 426, and an anode 427 are limited in this order. In this case, an n-channel TFT is fixed to the cathode 421. In FIG. 4A or 4B of this embodiment, the hole injecting layer, the hole transporting layer, the light-emitting layer, the electron transporting layer, and the electron injecting layer shown as a layer including a luminescent material. However, there is not always necessity to employ the structure, and an assistant layer such as a hole blocking layer or a mixed layer for which the above-mentioned respective layers are combined may be formed.

Embodiment 4

Figure 5:
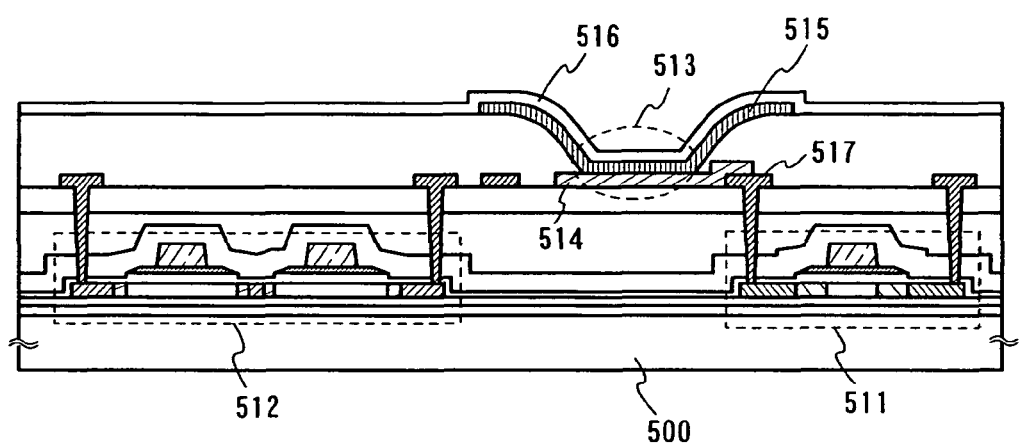
FIG. 5 is a diagram illustrating a light-emitting device.

In Embodiment 4, a light-emitting element is manufactured over a substrate 500 composed of a material such as glass, quartz, a metal, a bulk semiconductor, transparent plastic or flexible plastic. By manufacturing a plurality of light-emitting elements over a substrate like the light-emitting element described above, a passive matrix light-emitting device can be manufactured. In addition, other than the substrate composed of the material such as glass, quartz, transparent plastic, or flexible plastic, for example, as shown in FIG. 5, a light-emitting element in contact with a thin film transistor (TFT) array may be manufactured. In FIG. 5, TFTs 511 and 512 and a light-emitting element 513 that has an organometallic complex according to the present invention are manufactured. For the light-emitting element 513, a first electrode 514, a layer 515 including a luminescent material, and a second electrode 516 can be manufactured. Further, a wiring 517 is manufactured in contact with the second electrode 516. This structure makes it possible to manufacture an active matrix light-emitting device where driving of a light-emitting element is controlled by a TFT. It is to be noted that the structure of the TFT is not particularly limited. For example, a staggered TFT and an inverted staggered TFT may be used. In addition, the degree of crystallinity of a semiconductor layer forming the TFT is not particularly limited, either. A crystalline semiconductor layer or an amorphous semiconductor layer may be used.

EXAMPLES

Example 1

Example 1 is a synthesis example of an organometallic complex represented by the following structure formula (106) according to the present invention. This organometallic complex is an organometallic complex (hereinafter, abbreviated to Ir(dppr)$_2$(acac)) represented by a structure formula (70) in Table 6 described above, in which R$^2$=H, R$^3$=H, Ar=phenyl group, M=Ir, L is a monoanionic ligand having a β-diketone structure (represented by the structure formula (7)) in the general formula (17).

[formula 106]

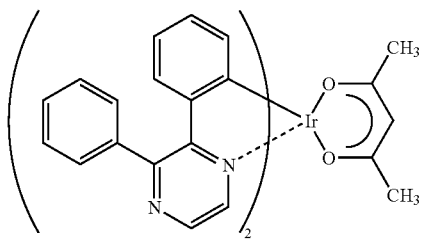

Ir(dppr)$_2$(acac)

<Step 1: Synthesis of Ligand Hdppr>

A ligand Hdppr itself to be used for the organometallic complex according to the present invention can be synthesized by a known method (refer to Japanese Patent Application Laid-Open No. 48-8788, for example). In the present example, a ligand Hdppr is synthesized according to the method described in Japanese Patent Application Laid-Open No. 48-8788. First, with the use of 300 mL of dehydrated ethanol as a solvent, 21.0 g (100 mmol) of benzyl and 6.1 g (101 mmol) of ethylenediamine are held at reflux in a nitrogen atmosphere for 6 hours. Further, the solution is condensed to one fifth, and a produced precipitation is collected. By washing the obtained precipitation with cool ethanol, 2,3-diphenyl-5,6-dihydropyrazine is obtained (yield: 78%).

Next, 18.3 g (78.2 mmol) of 2,3-diphenyl-5,6-dihydropyrazine and 4.4 g of potassium hydroxide are added to 200 mL of dissolved glycerin, and stirring with heating is performed at 190° C. for 20 minutes. After cooling, extraction with ether is performed several times, the ether is removed, and purification by column chromatography is performed with the use of an ethyl acetate/hexane solvent. By removing the ethyl acetate/hexane solvent, a ligand Hdppr (2,3-diphenylpyrazine) is obtained (apricot-orange powder, yield: 22%). The reactions in the step 1 are shown by a formula (107).

[formula 107]

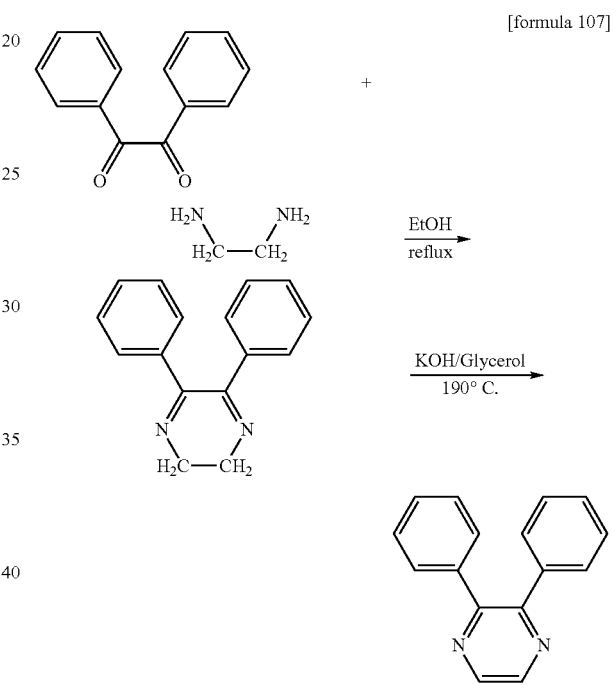

<Step 2: Synthesis of Dinuclear Complex [Ir(dppr)$_2$Cl]$_2$>

First, with the use of a mixture of 30 mL of 2-ethoxyethanol and 10 mL of water as a solvent, 1.86 g of the ligand Hdppr (2,3-diphenylpyrazine) and 0.96 g of iridium chloride (IrCl$_3$.HCl.H$_2$O) are mixed, and held at reflux for 17 hours in a nitrogen atmosphere to obtain a dinuclear complex [Ir(dppr)$_2$Cl]$_2$ (brown powder, yield: 10%). The reaction in the step 2 is shown by a formula (108).

[formula 108]

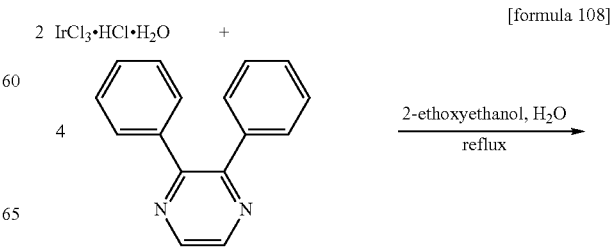

-continued

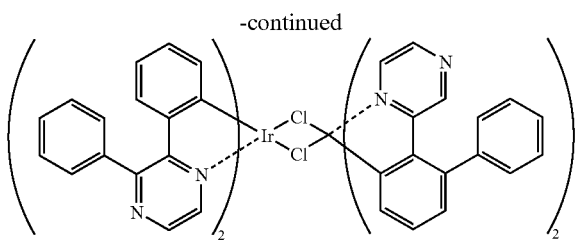

<Step 3: Synthesis of Organometallic Compound Ir(dppr)₂(acac) According to the Present Invention>

Further, with 30 mL of 2-ethoxyethanol as a solvent, 1.29 g of [Ir(dppr)₂Cl]₂, 0.29 mL of acetylacetone (Hacac), and 0.99 g of sodium carbonate are mixed, and held at reflux for 17 hours in a nitrogen atmosphere. A solution obtained by filtration of this is purified by column chromatography with the use of a dichloromethane solvent. Recrystallization is performed with the use of a dichloromethane/methanol solvent to obtain an organometallic compound Ir(dppr)₂(acac) according to the present invention (scarlet powder, yield: 10%). The reaction in the step 3 is shown by a formula (109).

[formula 109]

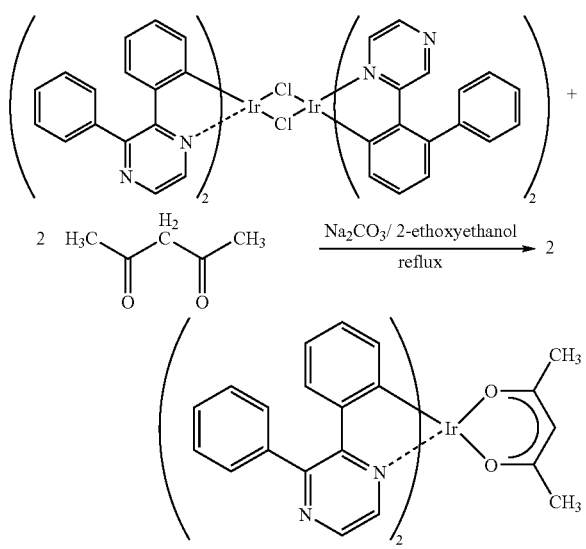

The organometallic compound, that is, the organometallic complex "Ir(dppr)₂(acac)" is analyzed by Nuclear Magnetic Resonance (¹H-NMR). The result of this analysis is as follows: ¹H-NMR δ (CDCl₃): 8.48 (d, 2H), 8.32 (d, 2H), 7.69 (m, 4H), 7.51 (m, 6H), 6.85 (d, 2H), 6.66 (t, 2H), 6.47 (t, 2H), 6.34 (d, 2H), 5.27 (s, 1H), 1.86 (s, 6H).

In addition, measurement of the thermal decomposition temperature $T_d$ of the obtained organometallic compound Ir(dppr)₂(acac) according to the present invention is performed by TG-DTA to find $T_d$=306° C., and it is determined that the organometallic complex shows favorable heat resistance.

Figure 6:
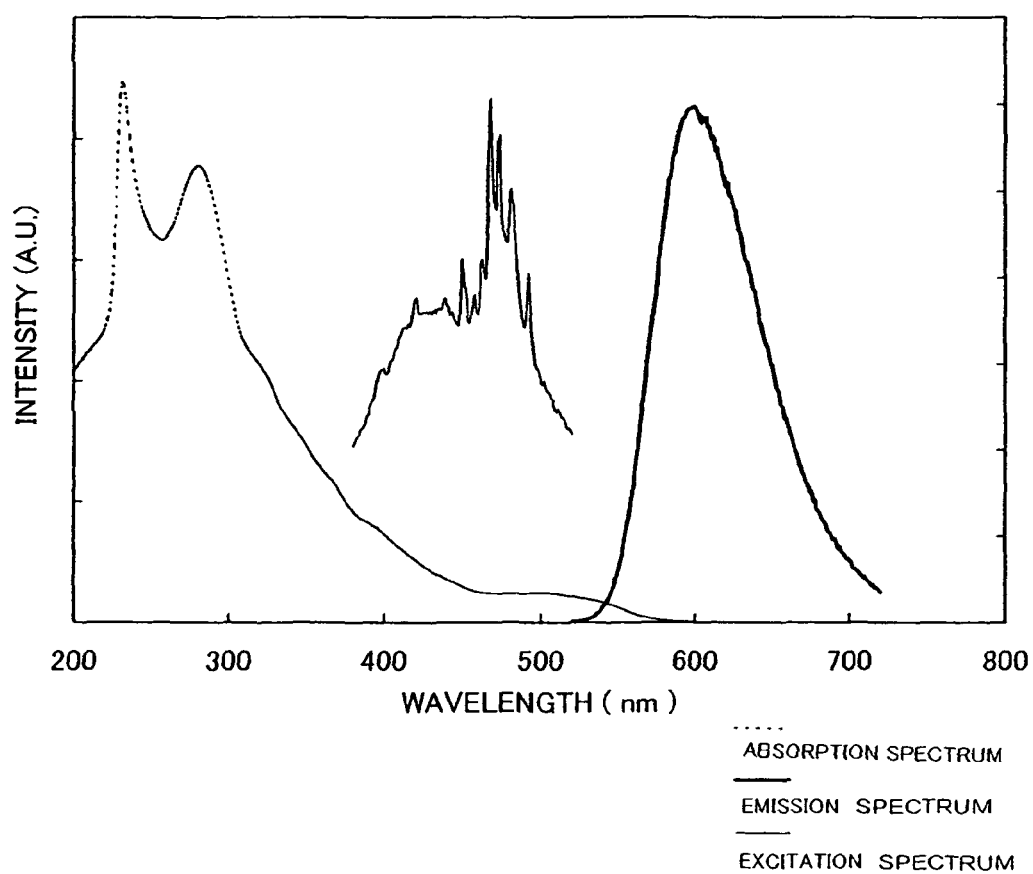
FIG. 6 is a diagram showing an UV-Vis absorption spectrum, an excitation spectrum, and an emission spectrum of an organometallic complex according to the present invention.

Next, FIG. 6 shows an absorption spectrum of Ir(dppr)₂(acac) in a dichloromethane solution, and an excitation spectrum and emission spectrum thereof at photoexcitation. It is to be noted that the absorption spectrum, the excitation spectrum, and the emission spectrum are indicated respectively by a dotted line, a thinner solid line, and a thicker solid line in the figure. The excitation spectrum is an excitation spectrum corresponding to an emission wavelength of 600 run. In addition, the emission spectrum is an emission spectrum obtained when Ir(dppr)₂(acac) is excited by the maximum peak (468 nm) of the excitation spectrum. Further, in FIG. 6, the vertical axis indicates intensity (arbitrary unit), and the horizontal axis indicates a wavelength (nm). The organometallic compound Ir(dppr)₂(acac) according to the present invention has absorption peaks at 231 nm, 281 nm, 320 nm, 400 nm, and 501 nm. In addition, the emission spectrum shows orange-red luminescence with an emission peak at 600 nm.

As described above, in the case of the organometallic complex Ir(dppr)₂(acac) according to the present invention, the several peaks are observed on the longer wavelength side. This is absorption unique to an organometallic complex as in the case of an orthometalated complex or the like, and is believed to correspond to singlet MLCT transition, triplet π-π* transition, triplet MLCT transition, and the like. In particular, the absorption peak at the longest wavelength side has a skirt shape broadly in the visible region, which is considered to be an absorption spectrum unique to triplet MLCT transition. Namely, it is determined that Ir(dppr)₂(acac) is a compound capable of direct photoexcitation to an excited triplet state and intersystem crossing.

In addition, luminescence derived from the compound is hardly observed when a dichloromethane solution of the organometallic compound Ir(dppr)₂(acac) according to the present invention is irradiated with light for substituting for oxygen (oxygen substitution), while luminescence is observed in the case of substituting for argon (argon substitution). This suggests that luminescence from the compound is phosphorescence.

Example 2

Figure 7:
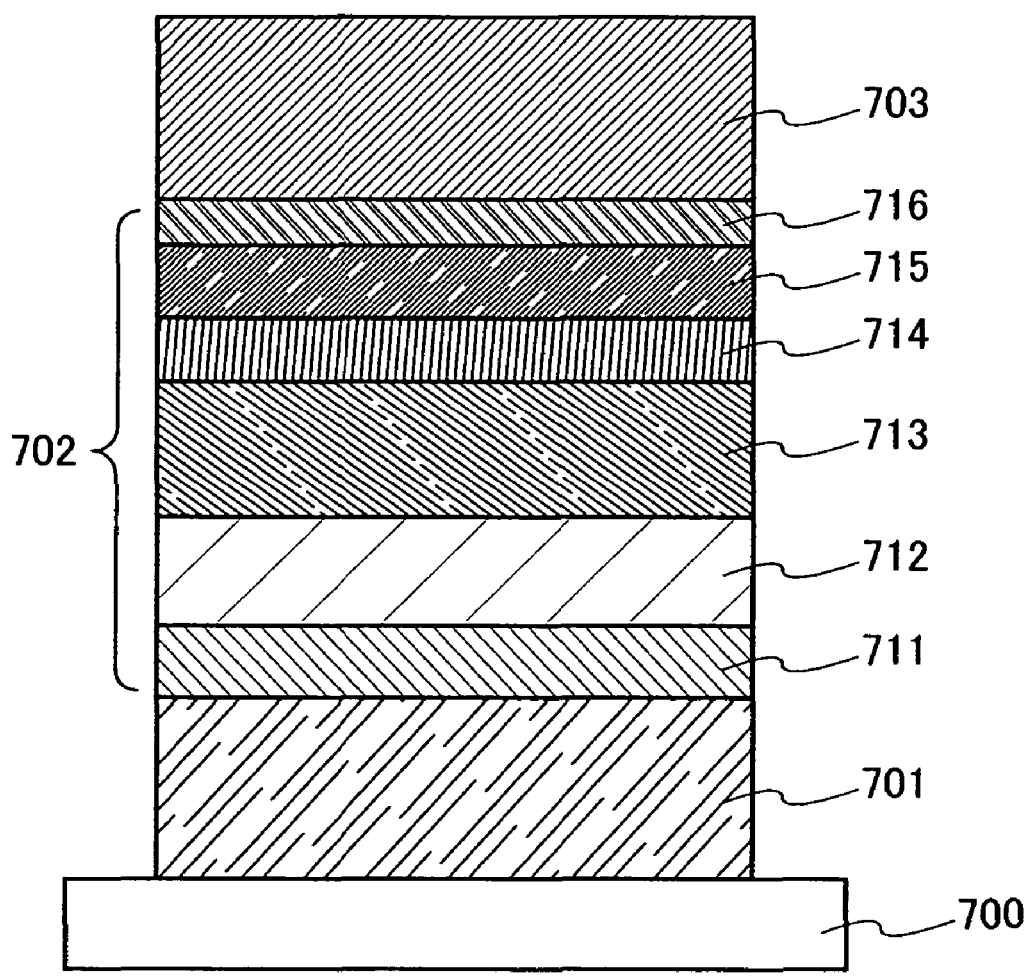
FIG. 7 is a diagram illustrating the structure of a light-emitting element using an organometallic complex according to the present invention.

In Example 2, a case of using an organometallic complex according to the present invention as a part of layer including a luminescent material to manufacture a light-emitting element, specifically, in the case of using an organometallic complex according to the present invention ass a guest material of a light-emitting element, the structure of an element will be described with reference to FIG. 7.

First, a first electrode 701 for a light-emitting element is formed over a substrate 700. In the present example, the first electrode 701 serves as an anode. With the use of ITO that is a transparent conductive film as a material, the first electrode 701 is formed by sputtering to be 110 nm in film thickness.

Next, a layer 702 including a luminescent material is formed on the first electrode (anode) 701. The layer 702 including the luminescent material in the present example has a laminated structure composed of a hole injecting layer 711, a hole transporting layer 712, a light-emitting layer 713, a hole blocking layer 714, an electron transporting layer 715, and an electron injecting layer 716.

The substrate over which the first electrode 701 is formed fixed in a substrate holder of a commercially produced vacuum deposition device with the surface at which the first electrode 701 is formed down, DNTPD is put in an evaporation source provided in the vacuum deposition device, and then, the hole injecting layer 711 is formed by evaporation using resistance heating to be 50 nm in film thickness. As a material for forming the hole injecting layer 711, a known hole injecting material can be used.

Then, a highly hole transporting material is used to form the hole transporting layer 712. As a material for forming the hole transporting layer 712, a known hole transporting material can be used. In the present example, with the use of α-NPD, the hole transporting layer 712 is formed in the same way to be 10 nm in film thickness.

Then, the light-emitting layer 713 is formed. In the light-emitting layer 113, a hole and an electron are recombined to generate luminescence. The light-emitting layer 713 formed in contact with the hole transporting layer 712 is formed with the use of a host material and a guest material that is an organometallic complex according to the present invention.

Specifically, with the use of CBP as the host material and Ir(dppr)$_2$(acac) as the guest material, the light-emitting layer 713 is formed by co-evaporation to be 30 nm in film thickness. The rate of the guest material is controlled to be 5.0 weight %.

Then, the hole blocking layer 714 is formed. As a material for forming the hole blocking layer 714, a known hole blocking material can be used. In the present example, with the use of BCP, the hole blocking layer 714 is formed by evaporation to be 10 nm in film thickness.

Then, the electron transporting layer 715 is formed. As a material for forming the electron transporting layer 715, a known electron transporting material can be used. In the present example, with the use of Alq$_3$, the electron transporting layer 715 is formed by evaporation to be 10 nm in film thickness.

Then, the electron injecting layer 716 is formed. As a material for forming the electron injecting layer 716, a known electron injecting material can be used. In the present example, with the use of CaF$_2$, the electron injecting layer 716 is formed by evaporation to be 2 nm in film thickness.

After forming the layer 702 including the luminescent material, which is formed by stacking the hole injecting layer 711, the hole transporting layer 712, the light-emitting layer 713, the hole blocking layer 714, the electron transporting layer 715, and the electron injecting layer 716 in this way, a second electrode 703 that serves as a cathode is formed by sputtering or evaporation. In the present example, aluminum 150 nm in film thickness is formed by evaporation on the layer 702 including the luminescent material to obtain the second electrode 703.

In this way, a light-emitting element using the organometallic complex according to the present invention is manufactured.

Figure 8:
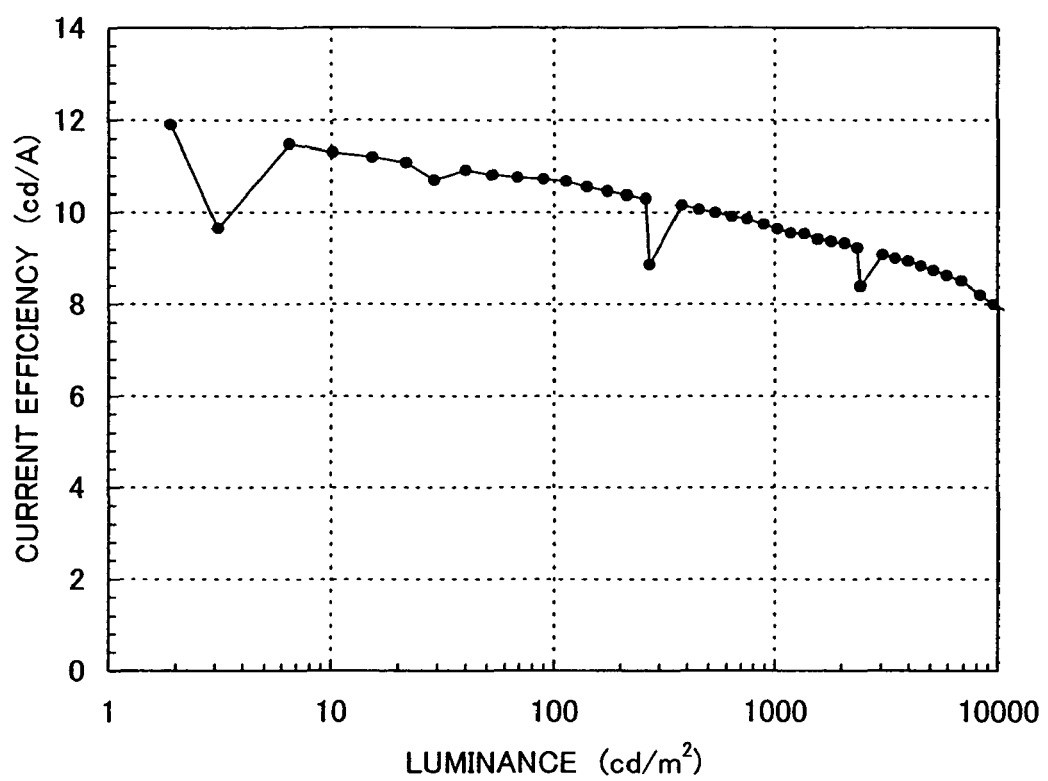
FIG. 8 is a diagram showing current efficiency-luminance characteristics of the light-emitting element using the organometallic complex according to the present invention.

When a voltage is applied to the formed light-emitting element, a luminance of 537 cd/m$^2$ is observed at 8.4 V, and the luminous efficiency at the applied voltage of 8.4 V is 10.0 cd/A. In addition, FIG. 8 shows current efficiency-luminance characteristics. Usually, in a light-emitting element using an organometallic complex in which intersystem crossing to the excited triplet state occurs, significant decrease in current efficiency is observed on a higher luminance side (a higher current region). However, decrease in current efficiency is hardly observed in the light-emitting element according to the present invention. Accordingly, the light-emitting element has the feature that a higher efficiency can be obtained also at a higher luminance.

Further, FIG. 9 shows an emission spectrum obtained when a voltage is applied to the light-emitting element to emit light with a luminance of 2000 cd/m$^2$. In FIG. 9, the vertical axis and the horizontal axis indicate EL (Electro Luminescence) intensity (arbitrary unit) and a wavelength (nm), respectively. As shown in FIG. 9, high-luminance orange-red luminescence with a peak at 601 nm can be obtained.

Example 3

In Example 3, an example of using an organometallic complex according to the present invention as a part of a layer including a luminescent material to manufacture a white light-emitting element will be described. The structure of the element will be described with reference to FIG. 10.

Since a substrate 800, a first electrode 801, and a second electrode 803 can be formed in the same way with the use of the same materials as those in Example 2, descriptions thereof are omitted.

A layer 802 including a luminescent material is formed by stacking a plurality of layers, by stacking a hole injecting layer 811, a hole transporting layer 812, a first light-emitting layer 813, a second light-emitting layer 814, a hole blocking layer 815, an electron transporting layer 816, and an electron injecting layer 817 in the present embodiment.

The hole injecting layer 811 is formed on the first electrode 801 with the use of a highly hole injecting material. As a material for forming the hole injecting layer 811, a known hole injecting material can be used. In the present example, with the use of Cu—Pc, the electron injecting layer 811 is formed by evaporation to be 20 nm in film thickness.

Then, the hole transporting layer 812 is formed. Since the hole transporting layer 812 can be formed to be 20 nm in film thickness in the same way with the use of the same material as that in Example 2, a description thereof is omitted.

Then, the first light-emitting layer 813 is formed. The first light-emitting layer 813 is formed with the use of a host material and a guest material.

Specifically, with the use of α-NPD as the host material and perylene as the guest material, the light-emitting layer 813 is formed by co-evaporation to be 10 nm in film thickness. The rate of the guest material is controlled to be 4.0 weight %.

Then, the second light-emitting layer 814 is formed. The second light-emitting layer 813 is formed with the use of a host material and a guest material that is an organometallic complex according to the present invention.

Specifically, with the use of BAlq as the host material and Ir(dppr)$_2$(acac) as the guest material, the host material is first evaporated to form 10 nm in film thickness, and the host material and the guest material are then co-evaporated to form a co-evaporated layer 10 nm in film thickness. The rate of the guest material is controlled to be 5.0 weight %.

Then, the hole blocking layer 815 is formed. As a material for forming the hole blocking layer 815, a known hole blocking material can be used. In the present example, with the use of BAlq, the hole blocking layer 814 is formed by evaporation to be 20 nm in film thickness.

Then, the electron transporting layer 816 is formed. Since the electron transporting layer 816 can be formed to be 20 nm in film thickness in the same way with the use of the same material as that in Example 2 as a material for forming the electron transporting layer 816, a description thereof is omitted.

Then, the electron injecting layer 817 is formed. Since the electron injecting layer 817 can be formed to be 1 nm in film thickness in the same way with the use of the same material as that in Example 2 as a material for forming the electron injecting layer 817, a description thereof is omitted.

Next, the second electrode 803 that serves as a cathode is formed by sputtering or evaporation. In the present example, aluminum 150 nm in film thickness is formed by evaporation on the layer 802 including the luminescent material to obtain the second electrode 803.

Thus, a white light-emitting element using the organometallic complex according to the present invention is manufactured. For example, since Ir(dppr)$_2$(acac) that is an example (refer to Example 1) of organometallic complexes according to the present invention shows orange-red luminescence with a higher luminance, it is quite effective apply Ir(dppr)₂(acac) to a white light-emitting element as described in the present example.

Example 4

In the present example, a light-emitting device that has a light-emitting element according to the present invention in a pixel portion will be described with reference to FIGS. 11A and 11B. FIG. 11A is a top view showing the light-emitting device and FIG. 8B is a cross-sectional view taken along line A-A' in FIG. 11A. Reference numeral 601 indicated by a dotted line denotes a driver circuit portion (a source side driver circuit), reference numeral 602 denotes a pixel portion, and reference numeral 603 denotes a driver circuit portion (a gate side driver circuit). In addition, reference numerals 604 and 605 denote a sealing substrate and a sealing material, respectively, and an inside 607 surrounded by the sealing material 605 is a space.

Reference numeral 608 is provided for transmitting signals to be input to the source side driver circuit 601 and the gate side driver circuit 603, and receives signals such as a video signal, a clock signal, a start signal, and a reset signal from FPC (Flexible Printed Circuit) 609 that serves as an external input terminal. Though only the FPC is shown in the figure here, a printed wiring board (PWB) may be attached to the FPC. The light-emitting device in the specification includes not only a light-emitting device body but also a state where an FPC or a PWB is attached thereto.

Next, the sectional structure will be explained with reference to FIG. 11B. The driver circuits and the pixel portion are formed over a substrate 610. The source side driver circuit 601 as the driver circuit portion and the pixel portion 602 are shown here.

In the source side driver circuit 601, a CMOS circuit is formed of a combination of an n-channel TFT 623 and a p-channel TFT 624. The TFTs forming the driver circuit may be formed of a known CMOS circuit, PMOS circuit, or NMOS circuit. Although the present example shows a driver integrated type in which a driver circuit is formed over a substrate, which is not always necessary, the driver circuit can be formed not over the substrate but outside the substrate.

The pixel portion 602 has a plurality of pixels, each including a switching TFT 611, a current controlling TFT 612, and a first electrode 613 electrically connected to a drain of the controlling TFT. In addition, an insulator 614 is formed to cover an edge of the first electrode 613. Here, a positive photosensitive acrylic resin film is used to form the insulator 614.

Besides, in order to obtain a favorable coverage, the insulator 614 is formed so that a top portion or bottom potion has a curved surface formed with a curvature. For example, in the case of using positive photosensitive acrylic as a material for the insulator 614, it is preferable that only a top portion of the insulator 614 have a curved surface with a curvature radius (0.2 μm to 3 μm). In addition, any of a negative photosensitive material that becomes insoluble in an etchant by light and a positive photosensitive material that becomes soluble in an etchant by light can be used as the insulator 614. Further, as a material for the insulator 614, inorganic substances can be used in addition to organic substances. For example, materials such as silicon oxide and silicon oxynitride can be used.

On the first electrode 613, a layer 616 including a luminescent material and a second electrode 617 are formed. Here, as a material to be used for the first electrode 613 that functions as an anode, it is preferable to use a material that has a large work function. For example, in addition to single layers such as a film composed of indium tin oxide, a film composed of indium tin oxide containing silicon oxide, a film composed of indium zinc oxide, a titanium nitride film, a chromium film, a tungsten film, a Zn film, and a Pt film, laminated structures such as a lamination layer of a titanium nitride film and a film including aluminum as its main component and a three-layer structure of a titanium nitride film, a film including aluminum as its main component, and a titanium nitride film can be used. When a laminated structure is employed, the wiring has a lower resistance, favorable ohmic contact can be taken, and it is possible to function as an anode.

The layer 616 including the luminescent material is formed by evaporation using an evaporation mask or by inkjet. The layer 616 including the luminescent material includes an organometallic complex according to the present invention. As a material to be used in combination with the organometallic complex, low molecular weight materials, middle molecular weight materials (including an oligomer and a dendrimer) or high molecular weight materials may be used. In addition, as a material to be used for the layer including the luminescent material, it is often the case that an organic material is used for a single layer or lamination layer. However, the present invention includes a structure in which an inorganic compound is used for a part of a film including an organic compound.

In addition, as a material to be used for the second electrode (cathode) 617 formed on the layer 616 including the luminescent material, a material that has a small work function (for example, Al, Ag, Li, Ca, Mg, In, an alloy thereof such as Mg:Ag, Mg:In, Al:Li, or CaF₂, or CaN) may be used. In the case of transmitting light generated in the layer 616 including the luminescent material through the second electrode 617, it is preferable to use a lamination layer of a metal thin film that has a thinned film thickness and a transparent conductive film (such as an indium oxide-tin oxide alloy (ITO), an indium oxide-zinc oxide alloy (In₂O₃—ZnO), or zinc oxide (ZnO)) as the second electrode (cathode) 617.

Further, the sealing substrate 604 and the substrate 610 are bonded with the sealing material 605 to have a structure where a light-emitting element 618 is provided in the space 607 surrounded by the substrate 610, the sealing substrate 604, and the sealing material 605. The space 607 also includes a structure of filling with the sealing material 605 in addition to a case of filling with an inert gas (such as nitrogen or argon).

It is preferable to use an epoxy resin for the sealing material 605. In addition, it is desirable to use a material that allows permeation of moisture or oxygen as little as possible. Further, as a material to be used for the sealing substrate 604, a plastic substrate including FRP (Fiberglass-Reinforced Plastics), PVF (polyvinylfluoride), Mylar, polyester, or acrylic can be used besides a glass substrate and a quarts substrate.

Example 5

In the present example, various electric apparatuses completed by using a light-emitting device that has a light-emitting element according to the present invention will be described with reference to FIGS. 12A to 12E.

As examples of electric apparatuses manufactured by using a light-emitting device formed according to the present invention, a television, a video camera, a digital camera, a goggle-type display (head mount display), a navigation system, a sound reproduction device (such as an in-car audio system or an audio set), a laptop personal computer, a game machine, a personal digital assistance (such as a mobile computer, a cellular phone, a portable game machine, or an electronic book), an image reproduction device equipped with a recording medium (specifically, a device equipped with a display device, which can reproduce a recording medium such as a digital versatile disc (DVD) and display the image), and a lighting apparatus can be given. FIGS. 12A to 12E show specific examples of these electric apparatuses.

Figure 12A:
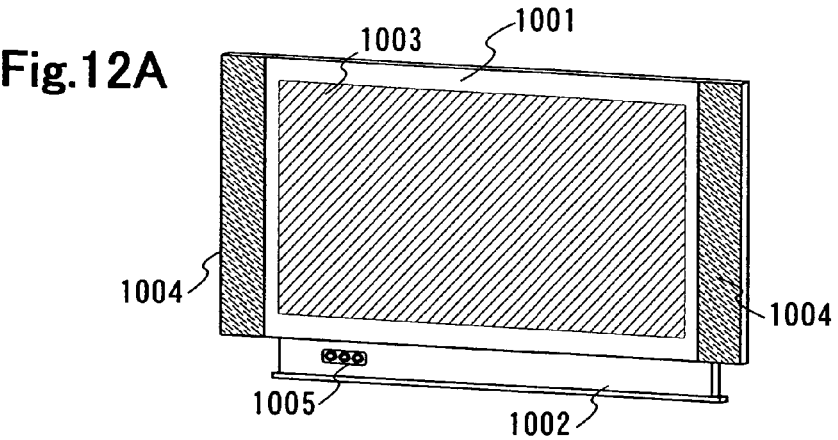
FIGS. 12A to 12E are diagrams illustrating electronic devices.

FIG. 12A is a display device, which includes a frame body 1001, a support 1002, a display portion 1003, a speaker portion 1004, and a video input terminal 1005. A light-emitting device formed according to the present invention is used for the display portion 1003 to manufacture the display device. The display device includes all devices for displaying information such as for a personal computer, for receiving TV broadcasting, and for displaying an advertisement.

Figure 12B:
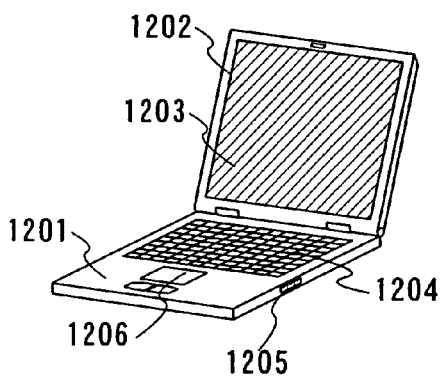

FIG. 12B is a laptop personal computer, which includes a main body 1201, a frame body 1202, a display portion 1203, a keyboard 1204, an external connection port 1205, and pointing mouse 1206. A light-emitting device that has a light-emitting element according to the present invention is used for the display portion 1203 to manufacture the laptop computer.

Figure 12C:
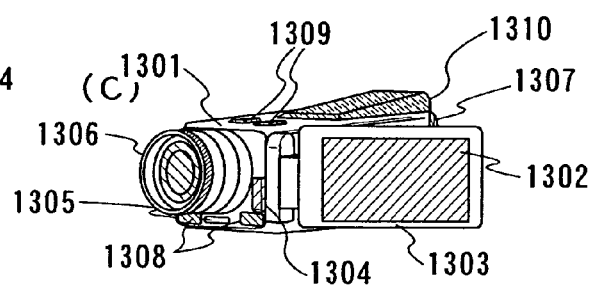

FIG. 12C is a video camera, which includes a main body 1301, a display portion 1, a frame body 1303, an external connection port 1304, a remote-control receiving portion 1305, an image receiving portion 1306, a battery 1307, a voice input portion 1308, operation keys 1309, and an eyepiece portion 1310. A light-emitting device that has a light-emitting element according to the present invention is used for the display portion 1302 to manufacture the video camera.

Figure 12D:
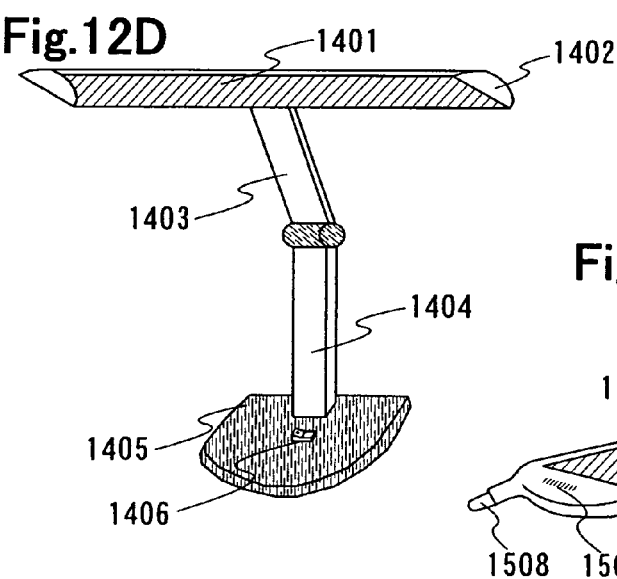

FIG. 12D is a desk lighting apparatus, which includes a lighting portion 1401, a shade 1402, a variable arm 1403, a support 1404, a pedestal 1405, and a power source 1406. A light-emitting device formed by using a light-emitting element according to the present invention is used for the display portion 1401 to manufacture the desk lighting apparatus. It is to be noted that the lighting apparatus includes a lighting apparatus to be fixed to the ceiling and a wall-hung lighting apparatus.

Figure 12E:
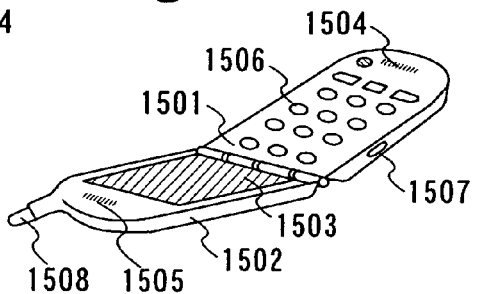

FIG. 12E is a cellular phone, which includes a main body 1501, a frame body 1502, a display portion 1503, a voice input portion 1504, a voice output portion 1505, an operation key 1506, an external connection port 1507, and an antenna 1508. A light-emitting device that has a light-emitting element according to the present invention is used for the display portion 1503 to manufacture the cellular phone.

As described above, an electric apparatus using a light-emitting device that has a light-emitting element according to the present invention can be obtained.

The light-emitting device shown in the present embodiment can be implemented by freely combining the structures of the light-emitting elements shown in Embodiments 2 and 3. Further, in the light-emitting device shown in the present embodiment, a color conversion film such as a color filter or a polarizing plate may be used if required.

Example 6

Example 6 is a synthesis example of an organometallic complex represented by the following structure formula (110) according to the present invention. This organometallic complex is an organometallic complex (abbreviation: Ir(bmppr)$_2$(acac)) in which R$^2$=H, R$^3$=H, Ar=4-methylphenyl group, M=Ir, L is a monoanionic ligand having a β-diketone structure (represented by the structure formula (7)) in the general formula (17).

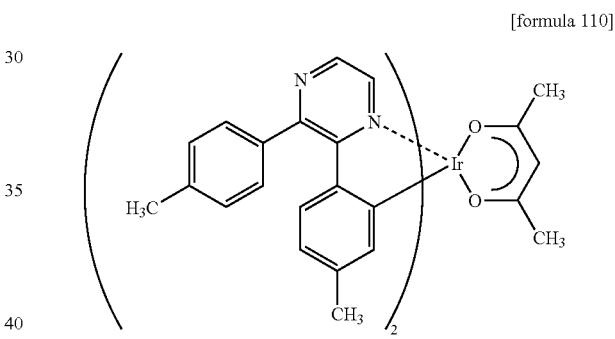

[formula 110]

<Step 1: Synthesis of Dinuclear Complex (abbreviation: [Ir(bmppr)$_2$Cl]$_2$)>

A ligand to be used for synthesis of the organometallic complex according to the present invention is 2,3-bis(4-methylphenyl)pyrazine (CAS number: 92405-82-8, abbreviation: Hbmppr). First, with a mixture of 60 mL of 2-ethoxyethanol and 20 mL of water as a solvent, 5.01 g of the ligand Hbmppr and 2.30 g of iridium chloride (IrCl$_3$.HCl.H$_2$O) are mixed and held at reflux for 16 hours in a nitrogen atmosphere to obtain a dinuclear complex [Ir(bmppr)$_2$Cl]$_2$ (brown powder, yield: 65%). The reaction in the step 1 is shown by a formula (111).

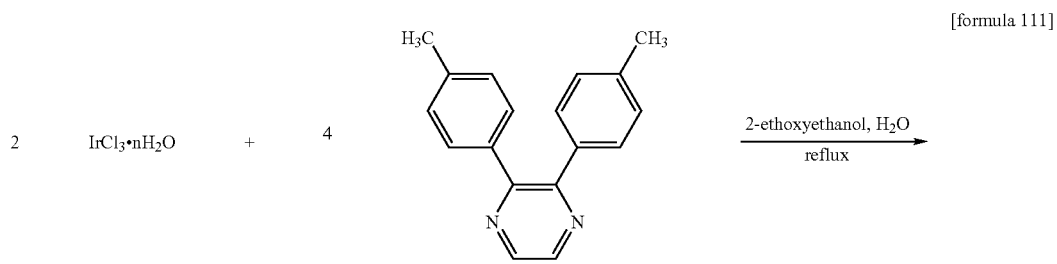

[formula 111]

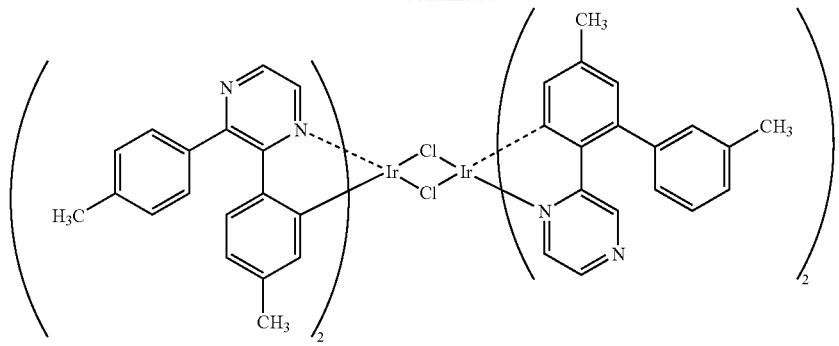

<Step 2: Synthesis of Organometallic Complex (abbreviation: [Ir(bmppr)$_2$(acac)]) According to the Present Invention>

Further, with 30 mL of 2-ethoxyethanol as a solvent, 1.85 g of the thus obtained [Ir(bmppr)$_2$Cl]$_2$, 0.38 mL of acethylacetone (abbreviation: Hacac), and 1.31 g of sodium carbonate are mixed, and held at reflux for 17 hours in a nitrogen atmosphere. A solution obtained by filtration of this is purified by column chromatography with the use of an ethyl acetate solvent. Recrystallization is performed with the use of a ethyl acetate/hexane solvent to obtain an organometallic compound Ir(bmppr)$_2$(acac) according to the present invention (brown powder, yield: 10%). The reaction in the step 2 is shown by a formula (112).

The organometallic compound, that is, the organometallic complex Ir(bmppr)$_2$(acac) is analyzed by Nuclear Magnetic Resonance ($^1$H-NMR). The result of this analysis is as follows: $^1$H-NMR δ (CDCl$_3$): 8.43 (d, 2H), 8.27 (d, 2H), 7.59 (d, 4H), 7.59 (m, 4H), 6.83 (d, 2H), 6.33 (d, 2H), 6.17 (s, 2H), 5.27 (s, 1H), 2.46 (s, 6H), 2.03 (s, 6H), 1.86 (s, 6H).

In addition, measurement of the thermal decomposition temperature T$_d$ of the obtained organometallic compound Ir(bmppr)$_2$(acac) according to the present invention is performed by a Thermogravimetry/Differential Thermal Analysis simultaneous measurement system (from Seiko Instruments Inc., TG/DTA) to find T$_d$=362° C., and it is determined that the organometallic complex shows favorable heat resistance.

Figure 13:
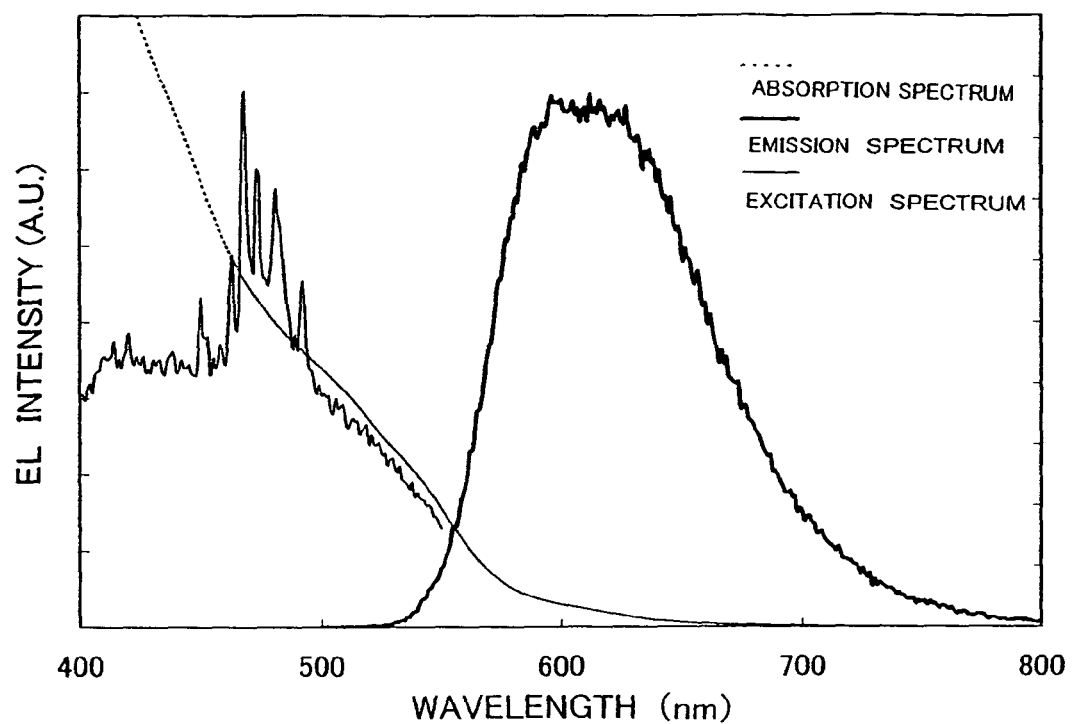
FIG. 13 is a diagram showing an UV-Vis absorption spectrum, an excitation spectrum, and an emission spectrum of an organometallic complex according to the present invention.

Next, FIG. 13 shows an absorption spectrum of Ir(bmppr)$_2$(acac) in dichloromethane, and an emission spectrum (PL: Photo Luminescence) and excitation spectrum thereof. The organometallic compound Ir(bmppr)$_2$(acac) according to the present invention has absorption peaks at 390 nm (sh), 440 nm (sh), 510 nm (sh), 400 nm, and 540 nm (sh). In addition, the emission spectrum shows orange luminescence that has intensity distribution in which the emission intensity is stronger from 600 to 615 nm. It is to be noted that the absorption spectrum, the excitation spectrum, and the emission spectrum are indicated respectively by a dotted line, a thinner solid line, and a thicker solid line in the figure.

In addition, the emission intensity of the organometallic compound Ir(bmppr)$_2$(acac) according to the present invention is examined under the condition that oxygen is dissolved in a dichloromethane solution including Ir(bmppr)$_2$(acac) before light irradiation and the condition that argon is dis-

[formula 112]

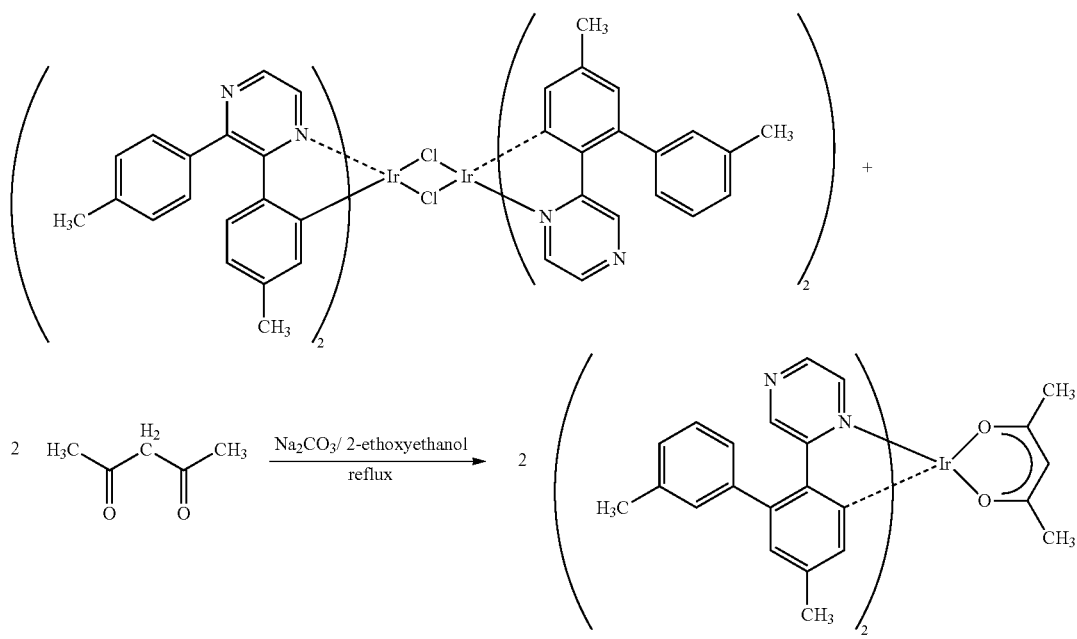

solved in a dichloromethane solution including Ir(bmppr)$_2$(acac) before light irradiation. In the result, Ir(bmppr)$_2$(acac) emits stronger light under the condition argon is dissolved, the same tendency as in the case of a phosphorescent material is observed. This result suggests that luminescence derived from the organometallic compound Ir(bmppr)$_2$(acac) according to the present invention is luminescence due to not fluorescence but phosphorescence.

Example 7

Figure 14:
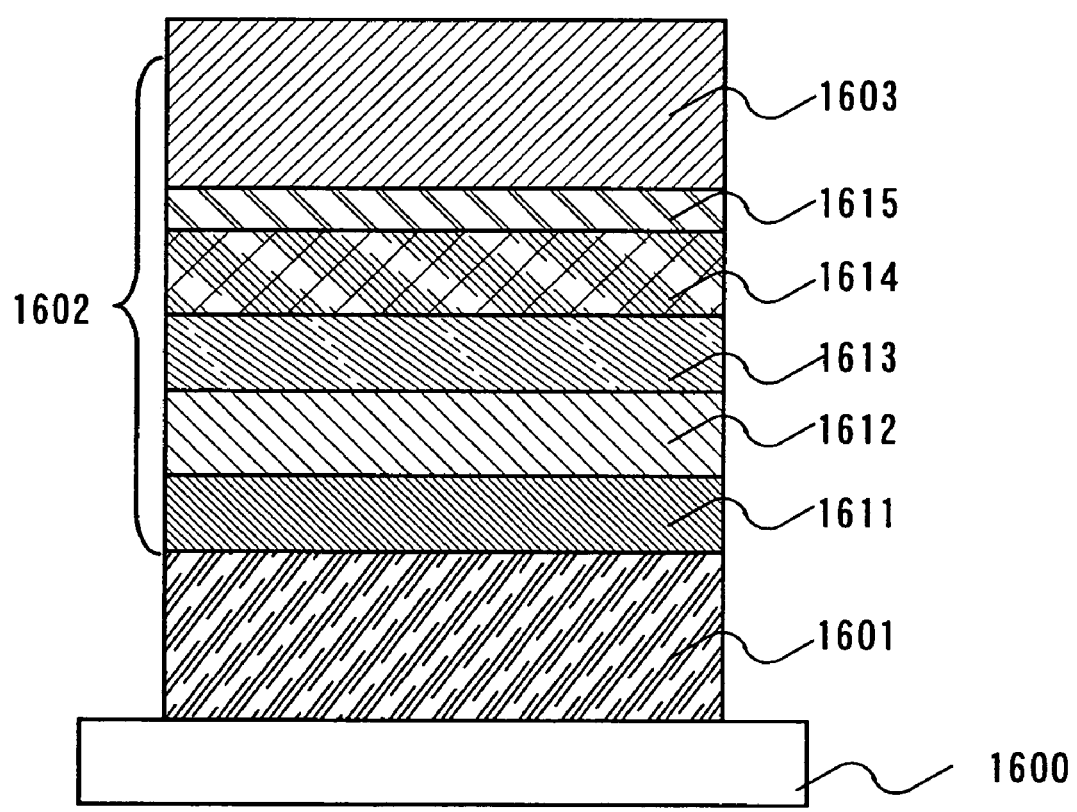
FIG. 14 is a diagram illustrating the structure of a light-emitting element using an organometallic complex according to the present invention.

In Example 7, a case of using an organometallic complex according to the present invention as a part of layer including a luminescent material to manufacture a light-emitting element, particularly, in the case of using an organometallic complex according to the present invention ass a guest material of a light-emitting element, the structure of an element will be described with reference to FIG. 14.

First, a first electrode 1601 for a light-emitting element is formed over a substrate 1600. In the present example, the first electrode 1601 serves as an anode. With the use of ITO including SiO$_2$ (a transparent conductive film) as a material, the first electrode 1601 is formed by sputtering to be 110 nm in film thickness.

Next, a layer 1602 including a luminescent material is formed on the first electrode (anode) 1601. The layer 1602 including the luminescent material in the present example is formed to have a laminated structure composed of a hole injecting layer 1611, a hole transporting layer 1612, a light-emitting layer 1613, an electron transporting layer 1614, and an electron injecting layer 1615.

The hole injecting layer 1611 is formed on the first electrode 1601. In the present example, with the use of Cu—Pc as a material for forming the hole injecting layer 1611, the hole injecting layer 1611 is formed by evaporation to be 20 nm in film thickness.

Then, the hole transporting layer 1612 is formed. In the present example, with the use of α-NPD as a material for forming the hole transporting layer 1612, the hole transporting layer 1612 is formed by evaporation to be 40 nm in film thickness.

Then, the light-emitting layer 1613 is formed with the use of a host material and a guest material that is an organometallic complex according to the present invention. Specifically, with the use of α-NPD as the host material and Ir(dppr)$_2$(acac) as the guest material, the light-emitting layer 1613 is formed by co-evaporation to be 30 nm in film thickness. The rate of the guest material is controlled to be 5 weight %. It is to be noted that the co-evaporation is a deposition method of evaporating each of a host material and a guest material by resistance heating and mixing them in the vapor phase.

Then, the electron transporting layer 1614 is formed. In the present example, BAlq and Alq$_3$ are used as materials for forming the electron transporting layer 1614 to form 10 nm in thickness and form 45 nm in film thickness thereon by evaporation.

Then, the electron injecting layer 1615 is formed. In the present example, with the use of CaF$_2$ as a material for forming the electron injecting layer 1615, the electron injecting layer 1615 is formed by evaporation to be 1 nm in film thickness.

After forming the layer 1602 including the luminescent material, which is formed by stacking the hole injecting layer 1611, the hole transporting layer 1612, the light-emitting layer 1613, the electron transporting layer 1614, and the electron injecting layer 1615 in this way, a second electrode 1603 that serves as a cathode is formed by sputtering or evaporation. In the present example, with the use of aluminum, the second electrode 1603 is formed by evaporation to be 150 nm in film thickness on the layer 1602 including the luminescent material.

In this way, a light-emitting element using the organometallic complex according to the present invention is manufactured.

Figure 17:
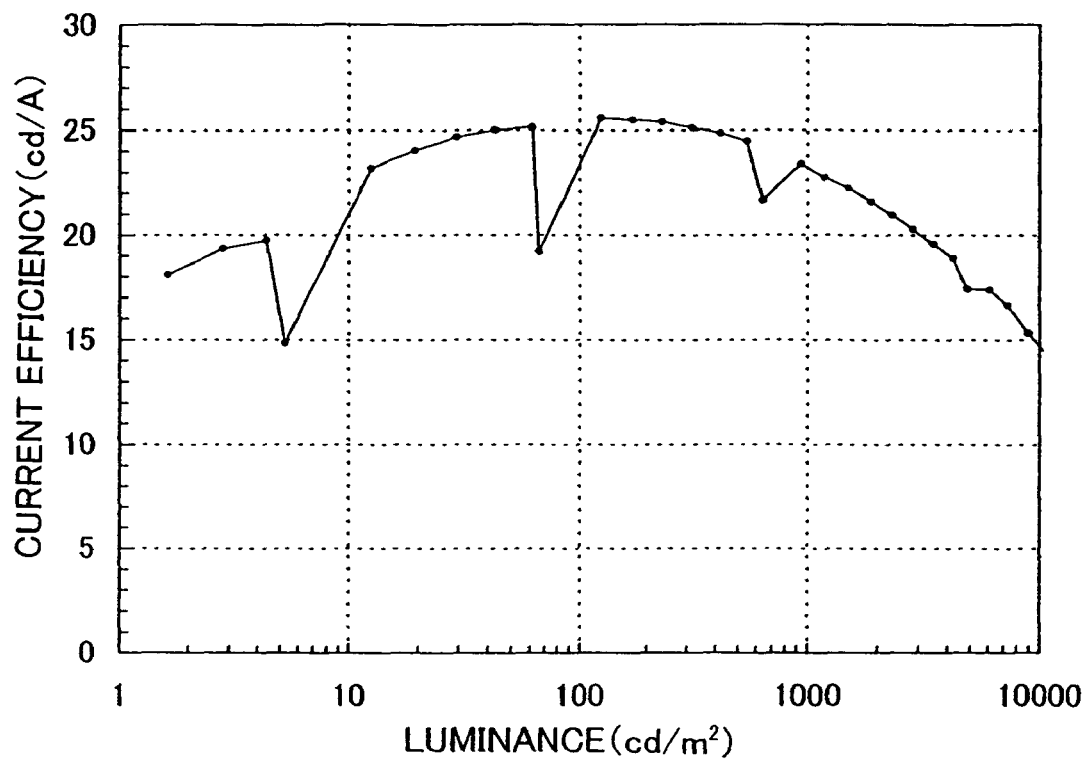
FIG. 17 is a diagram showing current efficiency-luminance characteristics of the light-emitting element using the organometallic complex according to the present invention.

When a voltage is applied to the manufactured light-emitting element, a luminance of 938 cd/m$^2$ is observed at 8.0 V, and the luminous efficiency at the applied voltage of 8.0 V is 23.4 cd/A. In addition, FIG. 17 shows current efficiency-luminance characteristics. Usually, in a light-emitting element using an organometallic complex in which intersystem crossing to the excited triplet state occurs, significant decrease in current efficiency is observed on a higher luminance side (a higher current region). However, decrease in current efficiency is hardly observed in the light-emitting element according to the present invention. Accordingly, the light-emitting element has the feature that a higher efficiency can be obtained also at a higher luminance.

Figure 20:
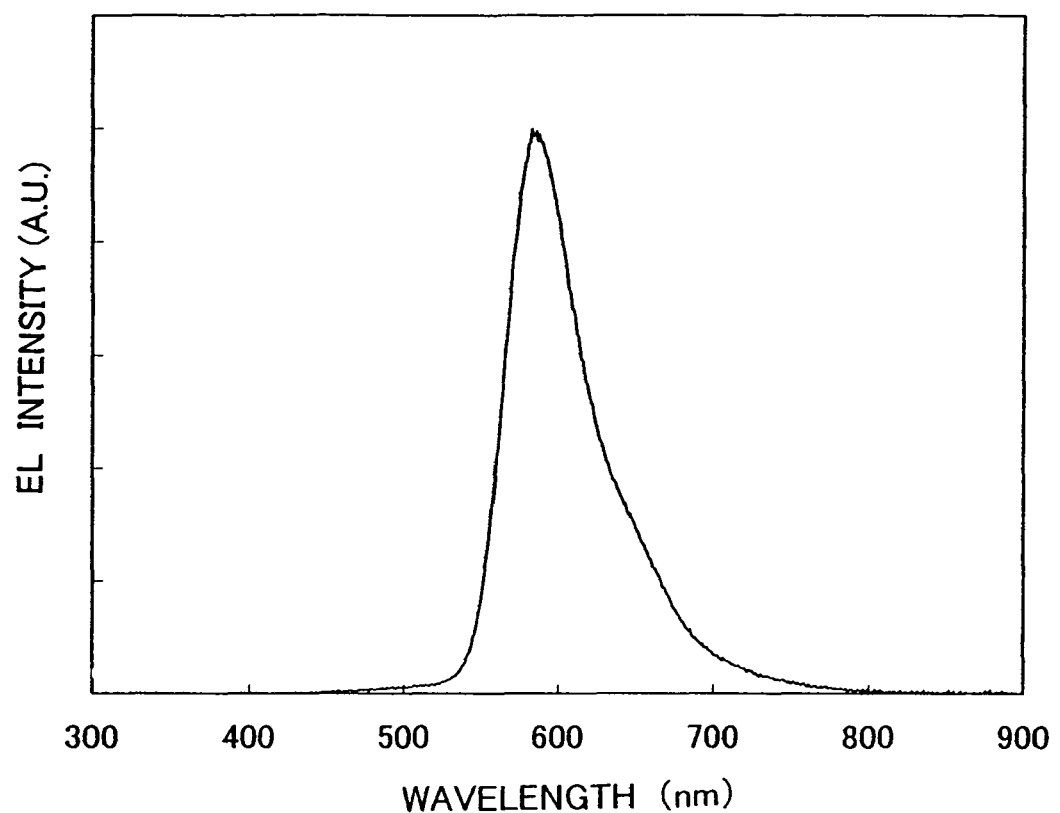
FIG. 20 is a diagram showing an emission spectrum of the light-emitting element using the organometallic complex according to the present invention.

Further, FIG. 20 shows an emission spectrum obtained when a voltage is applied to the light-emitting element to emit light with a luminance of 4500 cd/m$^2$. In FIG. 20, the vertical axis and the horizontal axis indicate EL (Electro Luminescence) intensity (arbitrary unit) and a wavelength (nm), respectively. As shown in FIG. 20, high-luminance orange-red luminescence with a peak at 583 nm can be obtained.

Example 8

Figure 15:
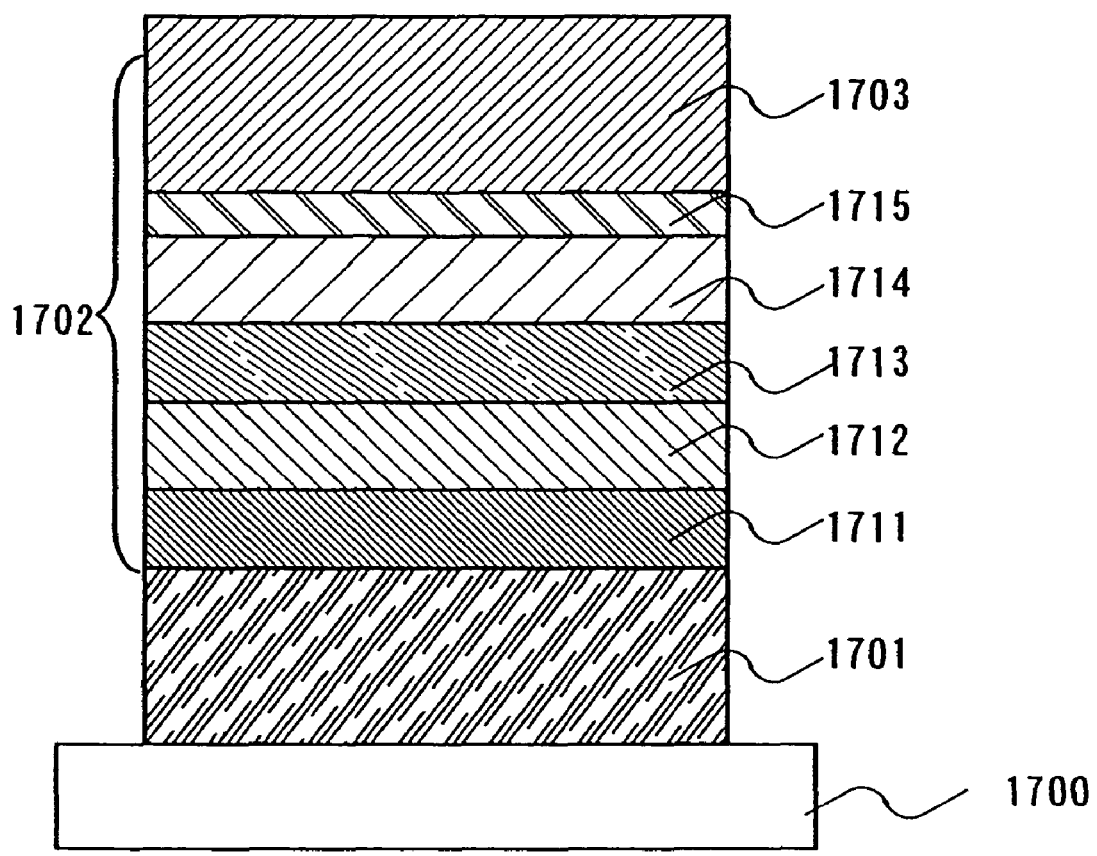
FIG. 15 is a diagram illustrating the structure of a light-emitting element using an organometallic complex according to the present invention.

In Example 8, a case of using an organometallic complex according to the present invention as a part of layer including a luminescent material to manufacture a light-emitting element, specifically, in the case of using an organometallic complex according to the present invention ass a guest material of a light-emitting element, the structure of an element will be described with reference to FIG. 15.

First, a first electrode 1701 for a light-emitting element is formed over a substrate 1700. In the present example, the first electrode 1701 serves as an anode. With the use of ITO including SiO$_2$ (a transparent conductive film) as a material, the first electrode 1701 is formed by sputtering to be 110 nm in film thickness.

Next, a layer 1702 including a luminescent material is formed on the first electrode (anode) 1701. The layer 1702 including the luminescent material in the present example is formed to have a laminated structure composed of a hole injecting layer 1711, a hole transporting layer 1712, a light-emitting layer 1713, an electron transporting layer 1714, and an electron injecting layer 1715.

The hole injecting layer 1711 is formed on the first electrode 1701. In the present example, with the use of Cu—Pc as a material for forming the hole injecting layer 1711, the hole injecting layer 1711 is formed by evaporation to be 20 nm in film thickness.

Then, the hole transporting layer 1712 is formed. In the present example, with the use of α-NPD as a material for forming the hole transporting layer 1712, the hole transporting layer 1712 is formed by evaporation to be 40 nm in film thickness.

Then, the light-emitting layer 1713 is formed with the use of a host material and a guest material that is an organometallic complex according to the present invention. Specifically, with the use of BAlq as the host material and Ir(dppr)$_2$(acac) as the guest material, the light-emitting layer 1713 is formed by co-evaporation to be 30 nm in film thickness. The rate of the guest material is controlled to be 5 weight %.

Then, the electron transporting layer 1714 is formed. In the present example, with the use of Alq$_3$ as a material for forming the electron transporting layer 1714, the electron transporting layer 1714 is formed by evaporation to be 50 nm in film thickness.

Then, the electron injecting layer 1715 is formed. In the present example, with the use of CaF$_2$ as a material for forming the electron injecting layer 1715, the electron injecting layer 1715 is formed by evaporation to be 1 nm in film thickness.

After forming the layer 1702 including the luminescent material, which is formed by stacking the hole injecting layer 1711, the hole transporting layer 1712, the light-emitting layer 1713, the electron transporting layer 1714, and the electron injecting layer 1715 in this way, a second electrode 1703 that serves as a cathode is formed by sputtering or evaporation. In the present example, with the use of aluminum, the second electrode 1703 is formed by evaporation to be 150 nm in film thickness on the layer 1702 including the luminescent material.

In this way, a light-emitting element using the organometallic complex according to the present invention is manufactured.

Figure 18:
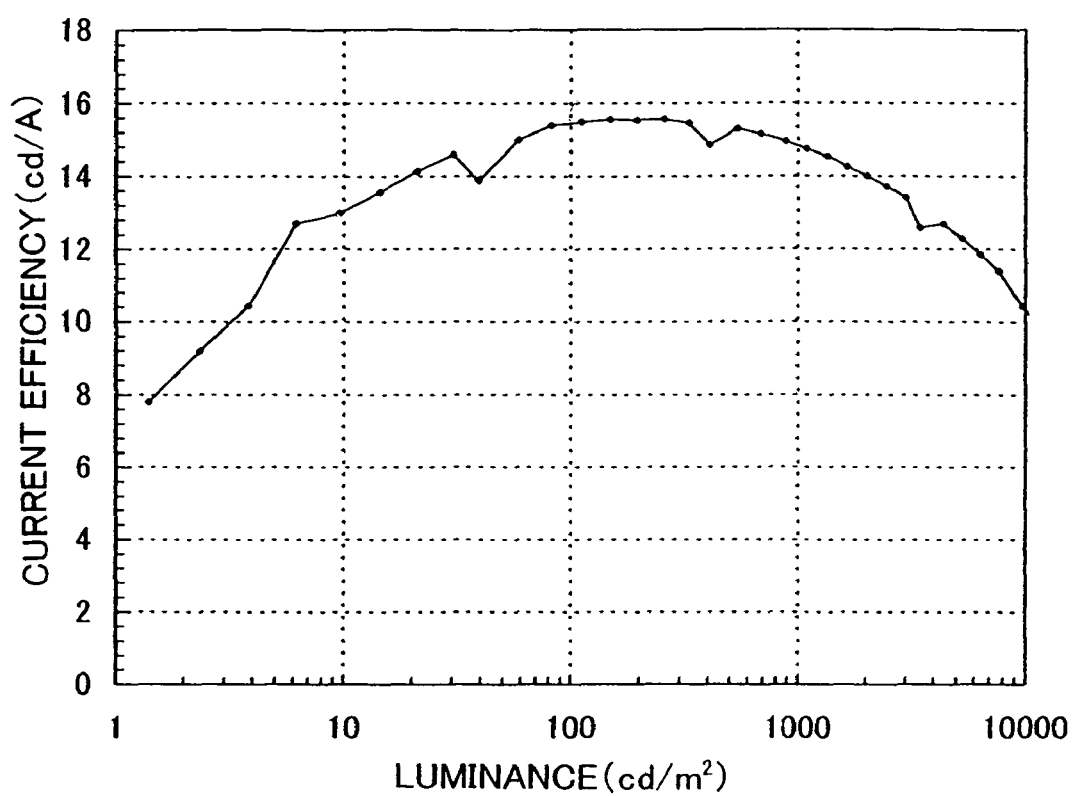
FIG. 18 is a diagram showing current efficiency-luminance characteristics of the light-emitting element using the organometallic complex according to the present invention.

When a voltage is applied to the manufactured light-emitting element, a luminance of 1090 cd/m$^2$ is observed at 9.8 V, and the luminous efficiency at the applied voltage of 9.8 V is 14.7 cd/A. In addition, FIG. 18 shows current efficiency-luminance characteristics. Usually, in a light-emitting element using an organometallic complex in which intersystem crossing to the excited triplet state occurs, significant decrease in current efficiency is observed on a higher luminance side (a higher current region). However, decrease in current efficiency is hardly observed in the light-emitting element according to the present invention. Accordingly, the light-emitting element has the feature that a higher efficiency can be obtained also at a higher luminance.

Figure 21:
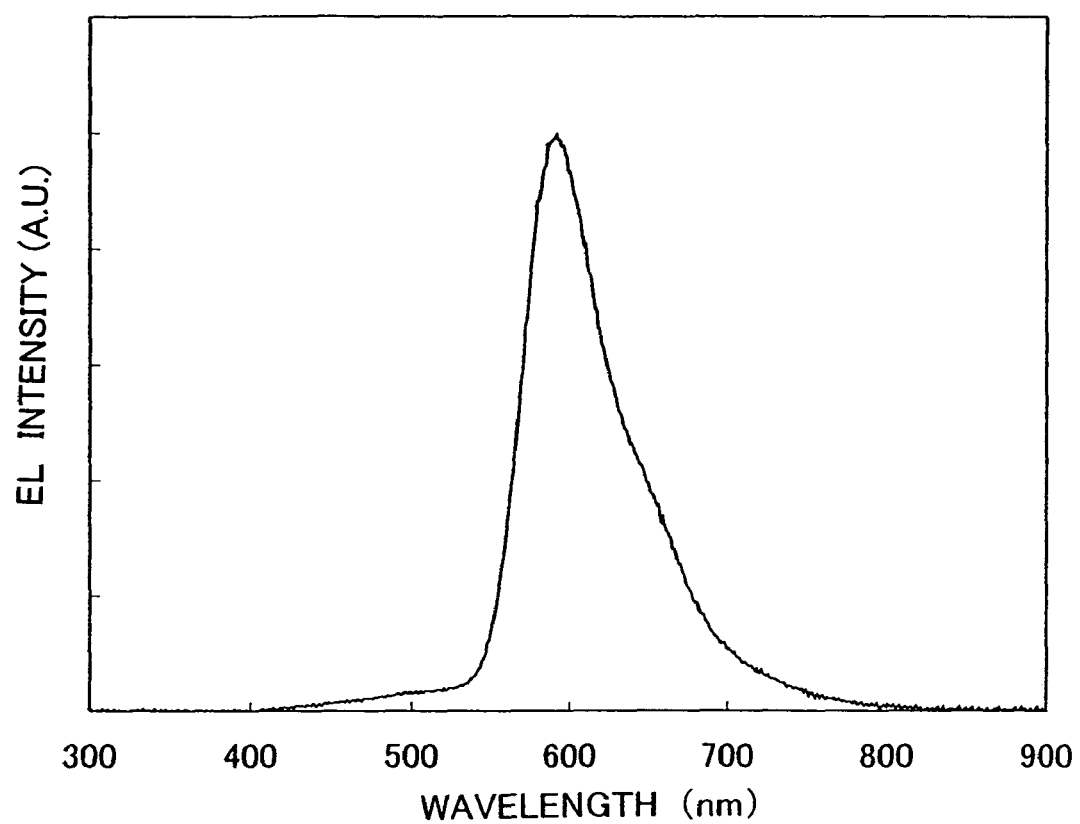
FIG. 21 is a diagram showing an emission spectrum of the light-emitting element using the organometallic complex according to the present invention.

Further, FIG. 21 shows an emission spectrum obtained when a voltage is applied to the light-emitting element to emit light with a luminance of 3200 cd/m$^2$. In FIG. 21, the vertical axis and the horizontal axis indicate EL (Electro Luminescence) intensity (arbitrary unit) and a wavelength (nm), respectively. As shown in FIG. 21, high-luminance orange-red luminescence with a peak at 592 nm can be obtained.

Example 9

Figure 16:
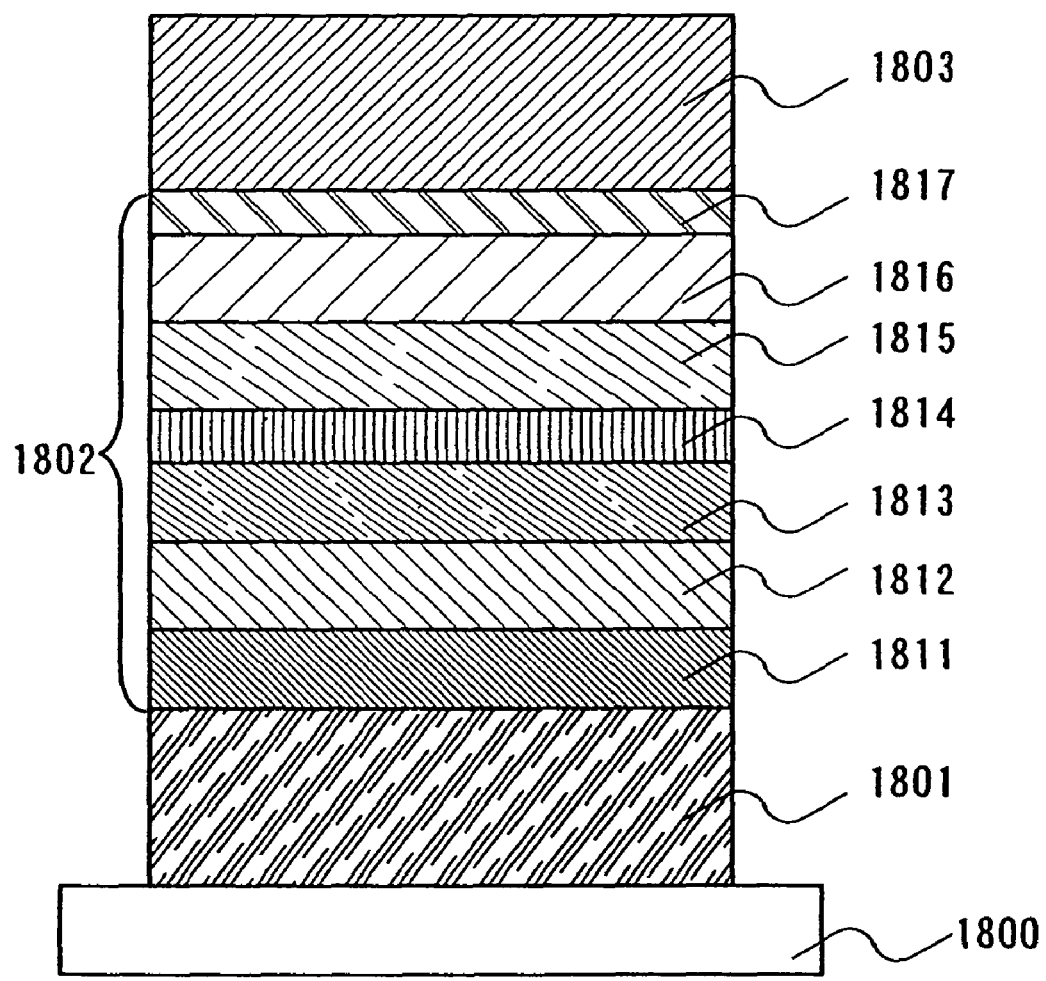
FIG. 16 is a diagram illustrating the structure of a light-emitting element using an organometallic complex according to the present invention.

In Example 9, an example of using an organometallic complex according to the present invention as a part of a layer including a luminescent material to manufacture a white light-emitting element will be described. The structure of the element will be described with reference to FIG. 16.

First, a first electrode 1801 for a light-emitting element is formed over a substrate 1800. In the present example, the first electrode 1701 serves as an anode. With the use of ITO including SiO$_2$ (a transparent conductive film) as a material, the first electrode 1801 is formed by sputtering to be 110 nm in film thickness.

Next, a layer 1802 including a luminescent material is formed on the first electrode (anode) 1801. The layer 1802 including the luminescent material in the present example is formed to have a laminated structure composed of a hole injecting layer 1811, a hole transporting layer 1812, a first light-emitting layer 1813, a blocking layer 1814, a second light-emitting layer 1815, an electron transporting layer 1816, and an electron injecting layer 1817.

The hole injecting layer 1811 is formed on the first electrode 1801. In the present example, with the use of Cu—Pc as a material for forming the hole injecting layer 1811, the hole injecting layer 1811 is formed by evaporation to be 20 nm in film thickness.

Then, the hole transporting layer 1812 is formed. In the present example, with the use of α-NPD as a material for forming the hole transporting layer 1812, the hole transporting layer 1812 is formed by evaporation to be 30 nm in film thickness.

Then, the first light-emitting layer 1813 is formed with the use of a host material and a guest material. Specifically, with the use of α-NPD as the host material and 2,5,8,11-tetra(tert-butyl)perylene (abbreviation: TBP) as the guest material, the light-emitting layer 1813 is formed by co-evaporation to be 20 nm in film thickness. The rate of the guest material is controlled to be 1 weight %.

Then, the blocking layer 1814 is formed. In the present example, with the use of BAlq as a material for forming the blocking layer 1814, the blocking layer 1814 is formed by evaporation to be 5.0 nm in film thickness.

Then, the second light-emitting layer 1815 is formed with the use of a host material and a guest material. Specifically, with the use of BAlq as the host material and Ir(dppr)$_2$(acac) as the guest material, the light-emitting layer 1813 is formed by co-evaporation to be 20 nm in film thickness. The rate of the guest material is controlled to be 5 weight %.

Then, the electron transporting layer 1816 is formed. In the present example, with the use of Alq$_3$ as a material for forming the electron transporting layer 1816, the electron transporting layer 1816 is formed by evaporation to be 30 nm in film thickness.

Then, the electron injecting layer 1817 is formed. In the present example, with the use of CaF$_2$ as a material for forming the electron injecting layer 1817, the electron injecting layer 1817 is formed by evaporation to be 1 nm in film thickness.

Next, the second electrode 1803 that serves as a cathode is formed by sputtering or evaporation. In the present example, with the use of aluminum, the second electrode 1803 is formed by evaporation to be 150 nm in film thickness on the layer 1802 including the luminescent material.

In this way, a light-emitting element using the organometallic complex according to the present invention is manufactured.

Figure 19:
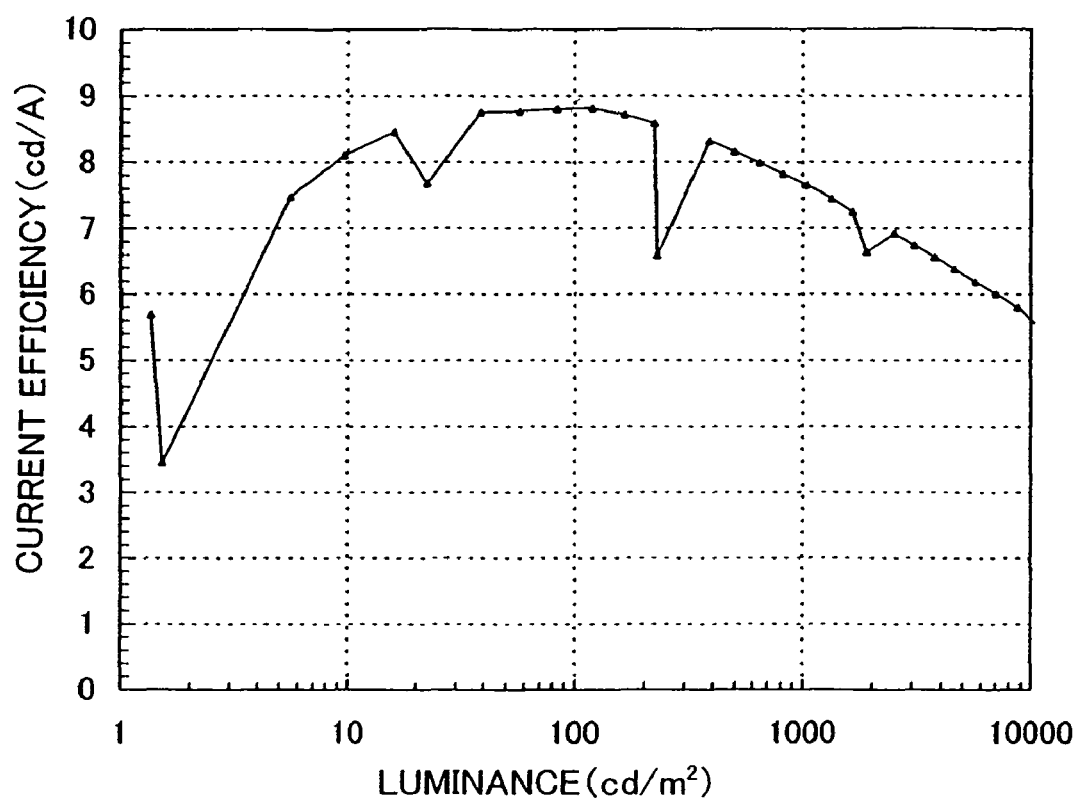
FIG. 19 is a diagram showing current efficiency-luminance characteristics of the light-emitting element using the organometallic complex according to the present invention.

When a voltage is applied to the manufactured light-emitting element, a luminance of 1040 cd/m$^2$ is observed at 8.6 V, and the luminous efficiency at the applied voltage of 8.6 V is 7.66 cd/A. In addition, FIG. 19 shows current efficiency-luminance characteristics. Usually, in a light-emitting element using an organometallic complex in which intersystem crossing to the excited triplet state occurs, significant decrease in current efficiency is observed on a higher luminance side (a higher current region). However, decrease in current efficiency is hardly observed in the light-emitting element according to the present invention. Accordingly, the light-emitting element has the feature that a higher efficiency can be obtained also at a higher luminance.

Figure 22:
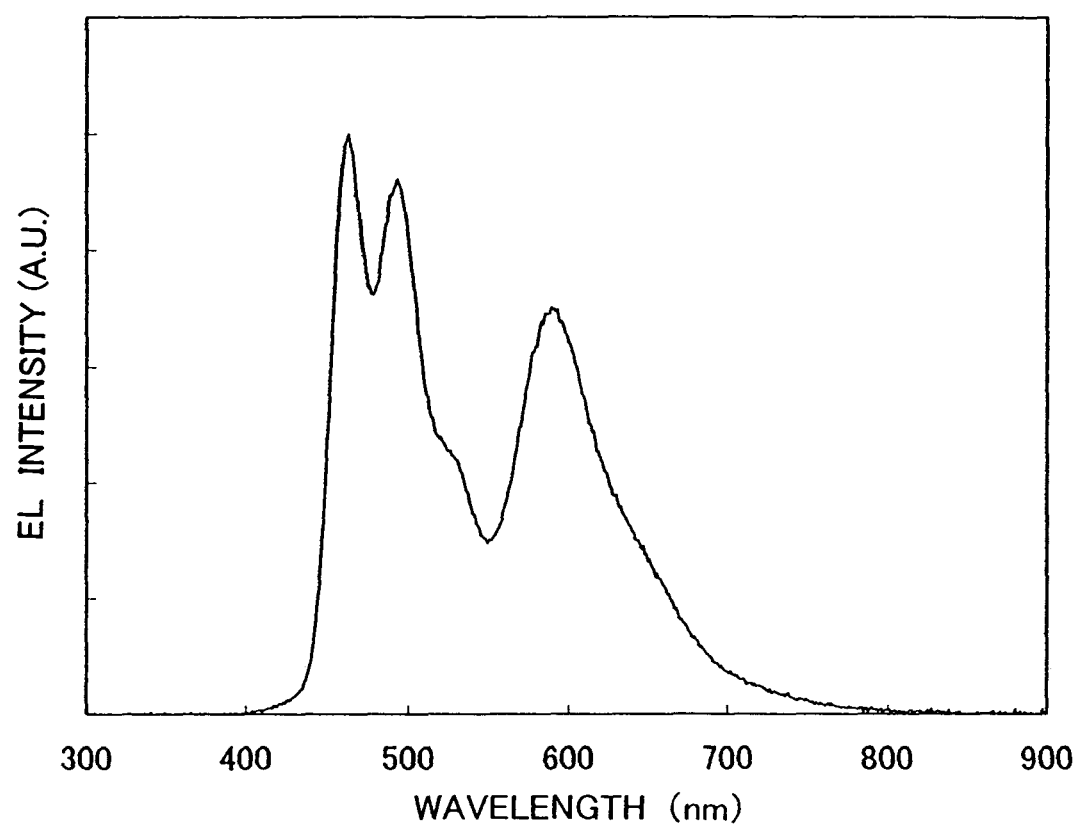
FIG. 22 is a diagram showing an emission spectrum of the light-emitting element using the organometallic complex according to the present invention.

Further, FIG. 22 shows an emission spectrum obtained when a voltage is applied to the light-emitting element to emit light with a luminance of 1700 cd/m$^2$. In FIG. 22, the vertical axis and the horizontal axis indicate EL (Electro Luminescence) intensity (arbitrary unit) and a wavelength (nm), respectively. As shown in FIG. 22, high-luminance white luminescence with a peak in each of a blue region, a green region and a red region can be obtained. Further, the CIE chromaticity coordinates in this case are (x, y)=(0.31, 0.34). The chromaticity coordinates hardly changes in the region of a lower luminance region (approximately 10 cd/m$^2$) to a higher luminance region (10000 cd/m²), and favorable white luminescence is shown in the large luminance region.

As described above, luminescence from Ir(dppr)₂(acac) and TBP can be extracted efficiently, and is visible as white luminescence as in the present example. Accordingly, application in the case of producing white luminescence as described in the present example is quite effective.

Although the present invention has been fully described by way of example with reference to the accompanying drawings, it is to be understood that various changes and modifications will be apparent to those skilled in the art. Therefore, unless such changes and modifications depart from the scope of the present invention hereinafter defined, they should be construed as being included therein.

What is claimed is:

1. An organometallic complex represented by the following general formula (4),

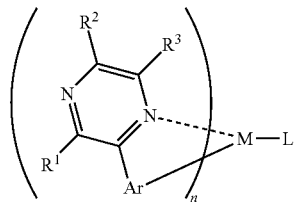

[formula 4]

wherein R¹ is an alkyl group,
wherein Ar is one of an aryl group having an electron-withdrawing group and a heterocyclic group having an electron-withdrawing group,
wherein R² and R³ are individually any one selected from the group consisting of a hydrogen atom, a halogen atom, an acyl group, an alkyl group, an alkoxyl group, an aryl group, a cyano group, and a heterocyclic group,
wherein M is one of an element of Group 9,
wherein n=2, and
wherein L is any one of a monoanionic ligand having a β-diketone structure, a monoanionic bidentate ligand having a carboxyl group, and a monoanionic bidentate ligand having a phenolic hydroxyl group.

2. The organometallic complex according to claim 1, the organometallic complex being represented by the following general formula (5),

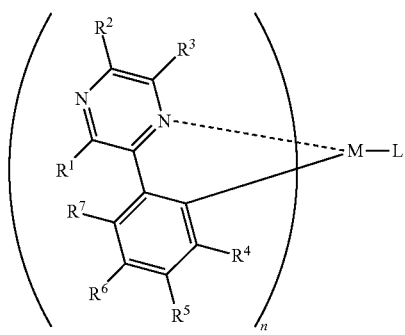

[formula 5]

wherein any one of R⁴ to R⁷ is an electron-withdrawing group, the others of R⁴ to R⁷ are individually any one selected from the group consisting of a hydrogen atom, a halogen atom, an acyl group, an alkyl group, an alkoxyl group, an aryl group, a cyano group, and a heterocyclic group.

3. The organometallic complex according to claim 1, the organometallic complex being represented by the following general formula (6),

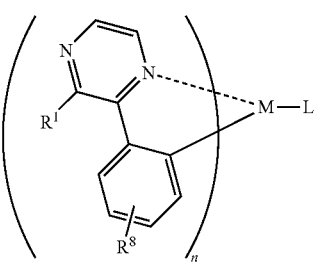

[formula 6]

wherein R⁸ is an electron-withdrawing group.

4. The organometallic complex according to claim 1,
wherein the L is any one of monoanionic bidentate ligands represented by the following structure formulas (7) to (13)

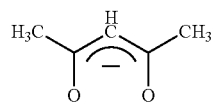

[formula 7]

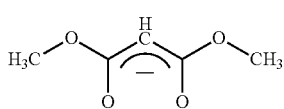

[formula 8]

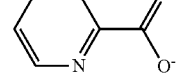

[formula 9]

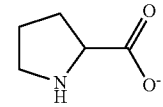

[formula 10]

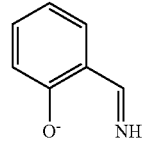

[formula 11]

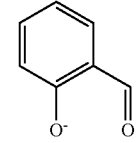

[formula 12]

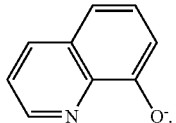

[formula 13]

5. An organometallic complex comprising a moiety represented by the following general formula (14),

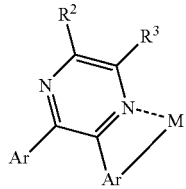
[formula 14]

wherein $R^2$ and $R^3$ are individually any one selected from the group consisting of hydrogen, a halogen atom, an acyl group, an alkyl group, an alkoxyl group, an aryl group, a cyano group, and a heterocyclic group, Ar is a heterocyclic group, and M is one of an element of Group 9 and an element of Group 10, and wherein Ar has an electron-withdrawing group.

6. An organometallic complex represented by the following general formula (17),

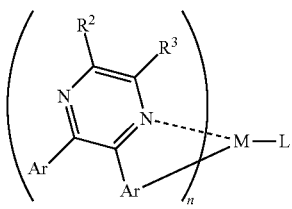
[formula 17]

wherein $R^2$ and $R^3$ are individually any one selected from the group consisting of hydrogen, a halogen atom, an acyl group, an alkyl group, an alkoxyl group, an aryl group, a cyano group, and a heterocyclic group, Ar is a heterocyclic group, M is one of an element of Group 9 and an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group.

7. The organometallic complex according to claim 6, wherein the L is any one of monoanionic bidentate ligands represented by the following structure formulas (7) to (13)

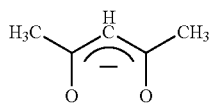
[formula 7]

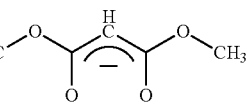
[formula 8]

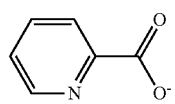
[formula 9]

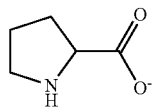
[formula 10]

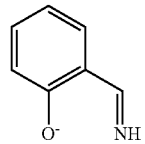
[formula 11]

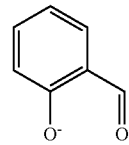
[formula 12]

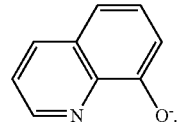
[formula 13]

8. The organometallic complex according to claim 7, wherein at least one of $R^2$ and $R^3$ is an electron-withdrawing group.

9. The organometallic complex according to claim 7, wherein Ar has an electron-withdrawing group.

10. The organometallic complex according to claim 7, wherein at least one of $R^2$ and $R^3$ is an electron-withdrawing group and Ar has an electron-withdrawing group.

11. The organometallic complex according to claim 5, wherein at least one of $R^2$ and $R^3$ is an electron-withdrawing group.

12. The organometallic complex according to claim 11, wherein the electron-withdrawing group which is selected from $R^2$ or $R^3$ or is had in Ar is one of a halogeno group and a haloalkyl group.

13. The organometallic complex according to claim 11, wherein the electron-withdrawing group which is selected from $R^2$ or $R^3$ or is had in Ar is one of a fluoro group and a trifluoromethyl group.

14. The organometallic complex according to claim 1, wherein the electron-withdrawing group is one of a halogen group and a haloalkyl group.

15. The organometallic complex according to claim 1, wherein the electron-withdrawing group is one of a fluoro group and a trifluoromethyl group.

16. The organometallic complex according to claim 6, wherein at least one of $R^2$ and $R^3$ is an electron-withdrawing group.

17. The organometallic complex according to claim 1, wherein the M is iridium.

18. The organometallic complex according to claim 5, wherein the M is one of iridium and platinum.

19. The organometallic complex according to claim 6, wherein the M is one of iridium and platinum.

20. A light-emitting element using the organometallic complex according to claim 1.

21. A light-emitting device using the light-emitting element according to claim 20.

22. An electric apparatus using the light-emitting element according to claim 20.

23. A light-emitting element using the organometallic complex according to claim 5.

24. A light-emitting device using the light-emitting element according to claim 23.

25. An electric apparatus using the light-emitting element according to claim 23.

26. A light-emitting element using the organometallic complex according to claim 6.

27. A light-emitting device using the light-emitting element according to claim 26.

28. An electric apparatus using the light-emitting element according to claim 26.

29. A light-emitting element using the organometallic complex according to claim 1 as a light emitter.

30. A light-emitting element using the organometallic complex according to claim 5 as a light emitter.

31. A light-emitting element using the organometallic complex according to claim 6 as a light emitter.

32. The organometallic complex according to claim 6, wherein Ar has an electron-withdrawing group.

33. The organometallic complex according to claim 6, wherein at least one of $R^2$ and $R^3$ is an electron-withdrawing group and Ar has an electron-withdrawing group.

34. The organometallic complex according to claim 1, wherein each of $R^1$ and $R^2$ is an alkyl group,
wherein the electron-withdrawing group is a fluoro group, and
wherein M is iridium.

* * * * *